United States Patent
Phillips

(10) Patent No.: US 6,213,947 B1
(45) Date of Patent: Apr. 10, 2001

(54) MEDICAL DIAGNOSTIC ULTRASONIC IMAGING SYSTEM USING CODED TRANSMIT PULSES

(75) Inventor: Patrick Phillips, Sunnyvale, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/283,346

(22) Filed: Mar. 31, 1999

(51) Int. Cl.[7] ........................................................ A61B 8/00

(52) U.S. Cl. ............................................ 600/443; 600/447

(58) Field of Search ..................................... 600/437, 443, 600/447; 73/625–626; 367/7, 11, 103–105

(56) References Cited

U.S. PATENT DOCUMENTS

| | | | |
|---|---|---|---|
| Re. 35,535 | * 6/1997 | Brumley et al. | 367/90 |
| 4,403,311 | 9/1983 | Tournois . | |
| 4,403,314 | 9/1983 | Tournois . | |
| 4,413,520 | * 11/1983 | Murakami et al. | 73/609 |
| 4,417,584 | * 11/1983 | Cathignol et al. | 600/454 |
| 4,456,982 | 6/1984 | Tournois . | |
| 4,458,342 | 7/1984 | Tournois . | |
| 4,815,043 | * 3/1989 | Shirasaka | 367/7 |
| 4,855,961 | * 8/1989 | Jaffe et al. | 367/7 |
| 5,014,712 | 5/1991 | O'Donnell . | |
| 5,022,400 | * 6/1991 | Walters | 600/455 |
| 5,142,649 | 8/1992 | O'Donnell . | |
| 5,224,482 | * 7/1993 | Nikoonahad et al. | 600/454 |
| 5,329,930 | * 7/1994 | Thomas, III et al. | 600/443 |
| 5,454,372 | 10/1995 | Banjnin et al. . | |
| 5,522,393 | 6/1996 | Phillips . | |
| 5,608,690 | 3/1997 | Hossack et al. . | |
| 5,675,554 | 10/1997 | Cole et al. . | |
| 5,851,187 | * 12/1998 | Thomas, III et al. | 600/447 |
| 5,938,611 | * 8/1999 | Muzilla et al. | 600/455 |
| 5,961,463 | * 10/1999 | Rhyne et al. | 600/458 |
| 5,964,706 | * 10/1999 | Ma et al. | 600/443 |
| 6,048,315 | * 4/2000 | Chiao et al. | 600/447 |

OTHER PUBLICATIONS

"Complementary Series," Marcel J.E. Golay, *IRE Transactions on Information Theory,* vol. IT 7, Jan. 1961, No. 1, pp. 82–87.

"Golay's Complementary Series", *IRE Transactions on Information Theory,* vol. IT–7, Oct., 1961, No. 4, pp. 273–276.

(List continued on next page.)

Primary Examiner—Francis J. Jaworski
(74) Attorney, Agent, or Firm—Brinks Hofer Gilson & Lione

(57) ABSTRACT

Coded transmit signals are used in medical diagnostic ultrasonic imaging systems. In one mode, first and second ultrasonic beams are launched into a body along first and second spatially distinct transmit beam directions and used with B-mode or motion detection processing. The two beams are coded with unique, preferably orthogonal, spatially invariant, nonlinear phase modulation codes and the second beam is launched before the first beam has left the tissue. The first and second transmit beams may be included in a single transmit event. Frame rates are improved. Multiple spectral Doppler images from independent gates are generated. In another mode, first and second uniquely coded ultrasonic beams are launched into a body to focus at substantially the same point such that the two beams sample motion at different times. Unconventionally high velocity parameters are estimated and other motion parameters, including velocity parameters, may be estimated with improved accuracy. In yet another mode, first and second uniquely coded ultrasonic beams are launched into a body to focus preferentially at the same point where each beam originates from a subaperture and the receive signals are used with motion detection processing. Improved direction sensitivity to motion is obtained. In yet another mode, two or more coded ultrasonic beams are launched into the body with alternating polarities in a pulse inversion harmonic Doppler mode to improve the SNR while imaging contrast agents.

109 Claims, 23 Drawing Sheets

OTHER PUBLICATIONS

"Properties of Swept FM Waveforms in Medical Ultrasound Imaging," C.R. Cole, Acuson Corporation, Mountain View, California.

"Acoustical Imaging Via Coherent Reception of Spatially Coloured Transmissions," P. Tournois, 1980 IEEE, 1980 Ultrasonics Symposium, pp. 747–750.

"Multibeam Imaging Using Spatially Variant Insonification," Jules S. Jaffe and Phillipe M. Cassereau, *J. Acoust. Soc. Am. 83* (4), Apr. 1988, pp. 1458–1464.

"Coded Excitation System for Improving the Penetration of Real–Time Phased–Array Imaging Systems," Matthew O'Donnell, *IEEE Transactions on Ultrasonics, Ferroelectrics, and Frequency Control,* vol. 39, No. 3, May 1992, pp. 341–351.

"Filter–Based Coded–Excitation System for High–Speed Ultrasonic Imaging," Jian Shen and Emad S. Ebbini, *IEEE Transactions on Medical Imaging,* vol. 17, No. 6, Dec. 1998, pp. 923–934.

"Coded Excitation for Harmonic Imaging," Y. Takeuchi, Ultrasonics, PH–3, 1996.

"Chirped Excitation for <–100dB Time Sidelobe Echo Sounding," Y. Takeuchi.

"Simultaneous MultiFrequency Ultrasonography The Principle and Technology," Miwa et al., 1981 Ultrasonics Symposium, pp. 655–659.

"Echography Using Correlation Techniques: Choice of Coding Signal," Benkhelifa et al., 1994 IEEE, pp. 579–587.

"Real–Time Two–Dimensional Doppler Flow Mapping Using Auto–Correlation," C. Kasai et al., pp. 447–460.

"Radar Signals, an Introduction to Theory and Application," C. Cook et al., Chapter 3.

* cited by examiner

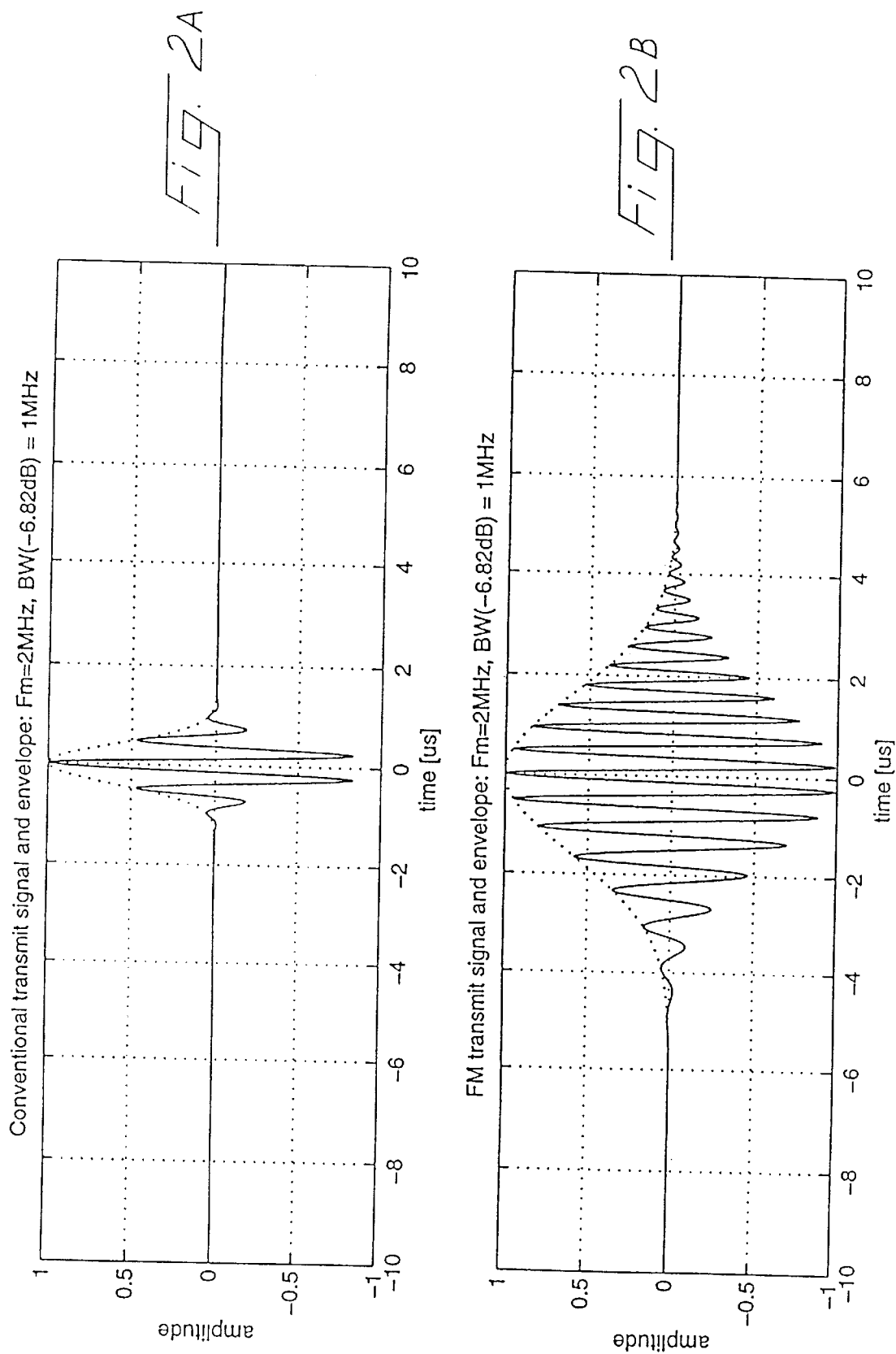

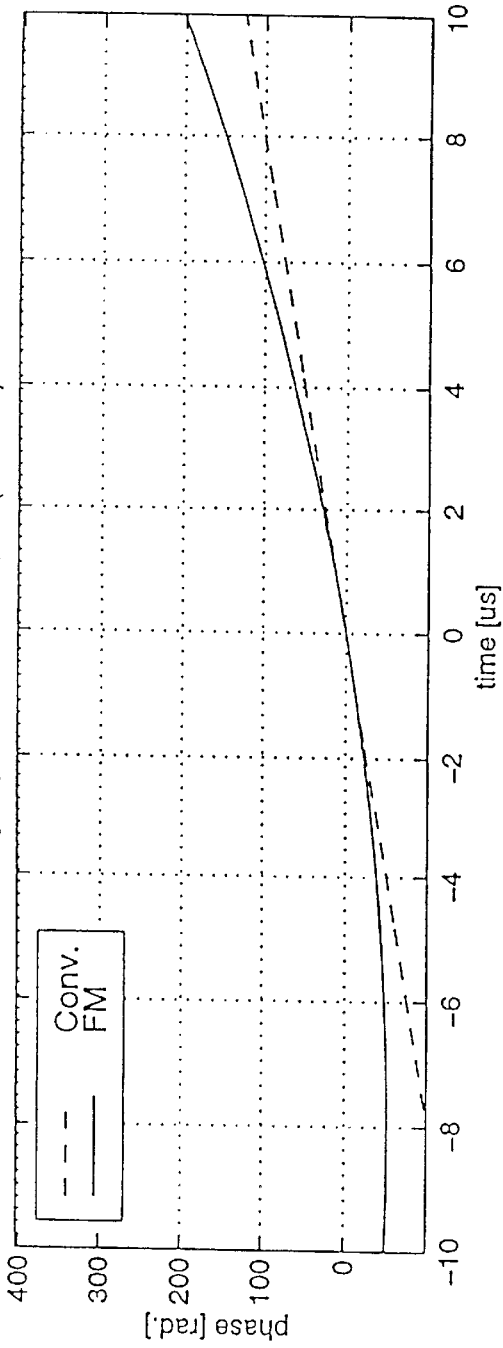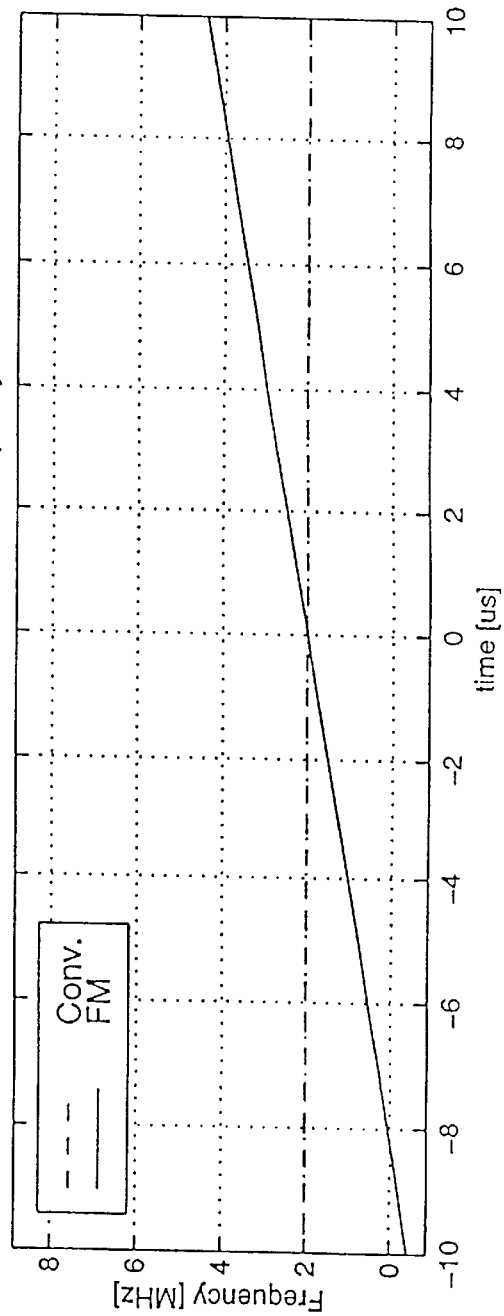

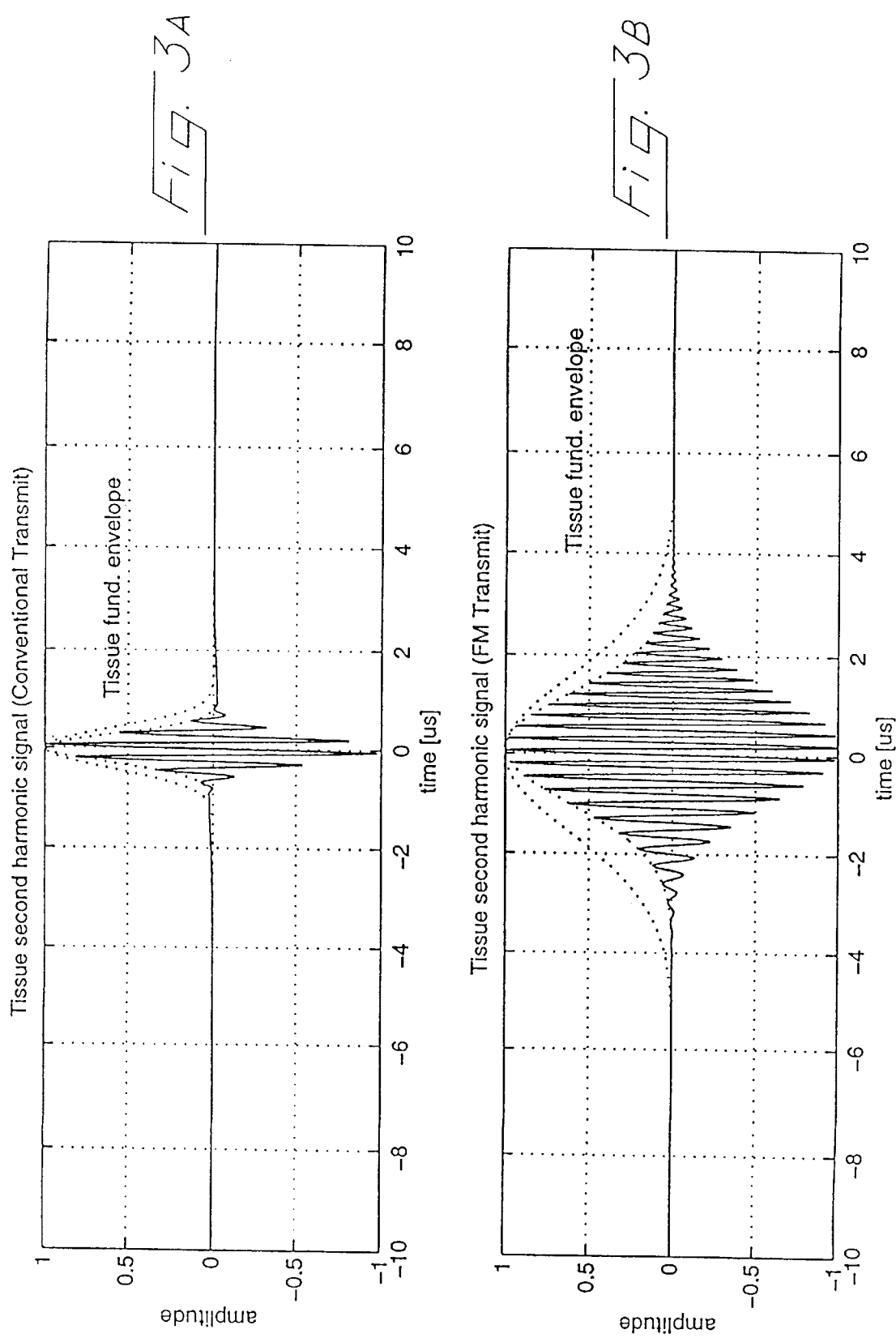

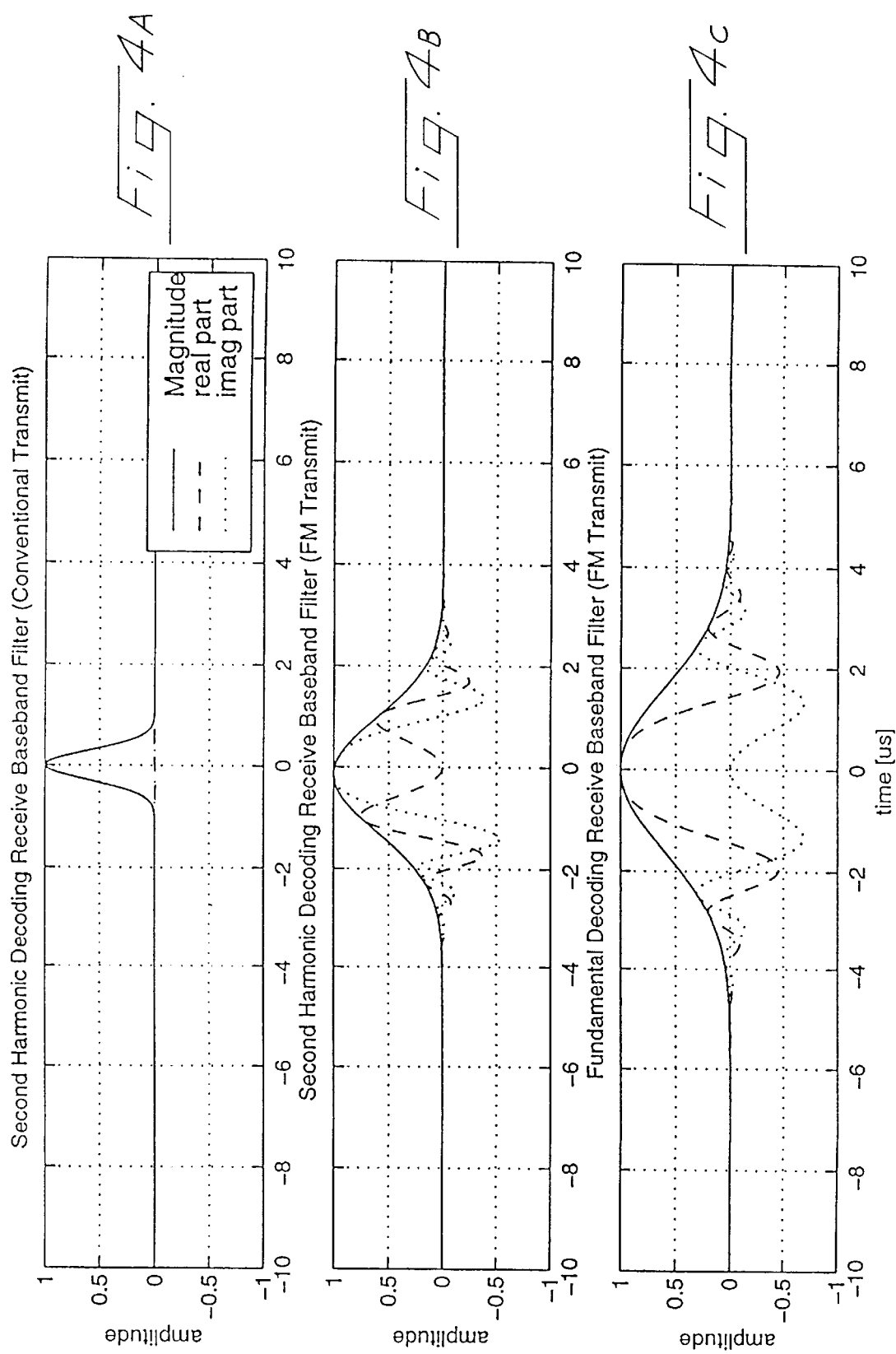

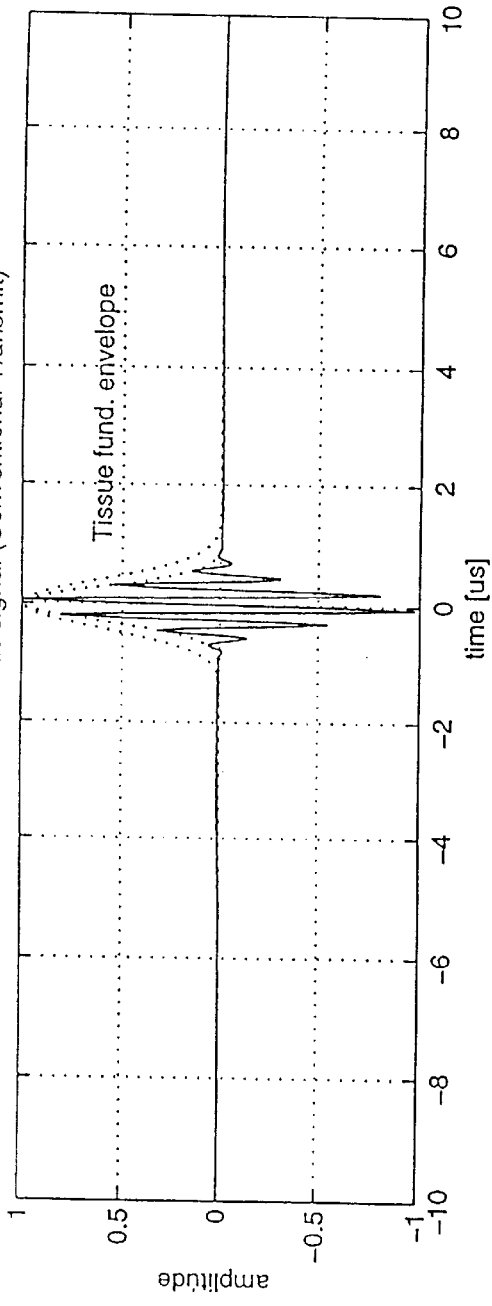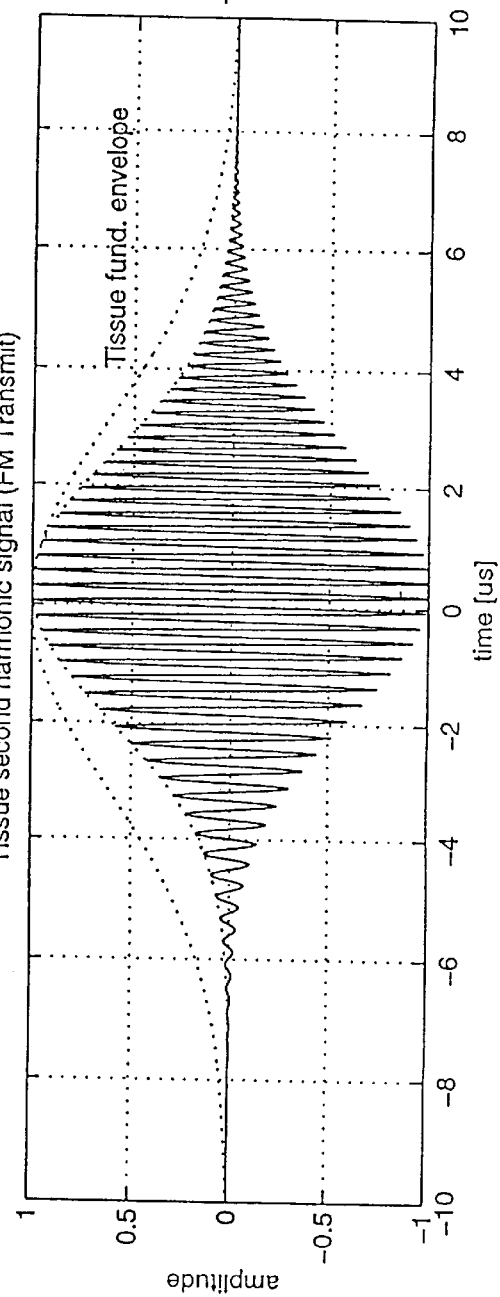

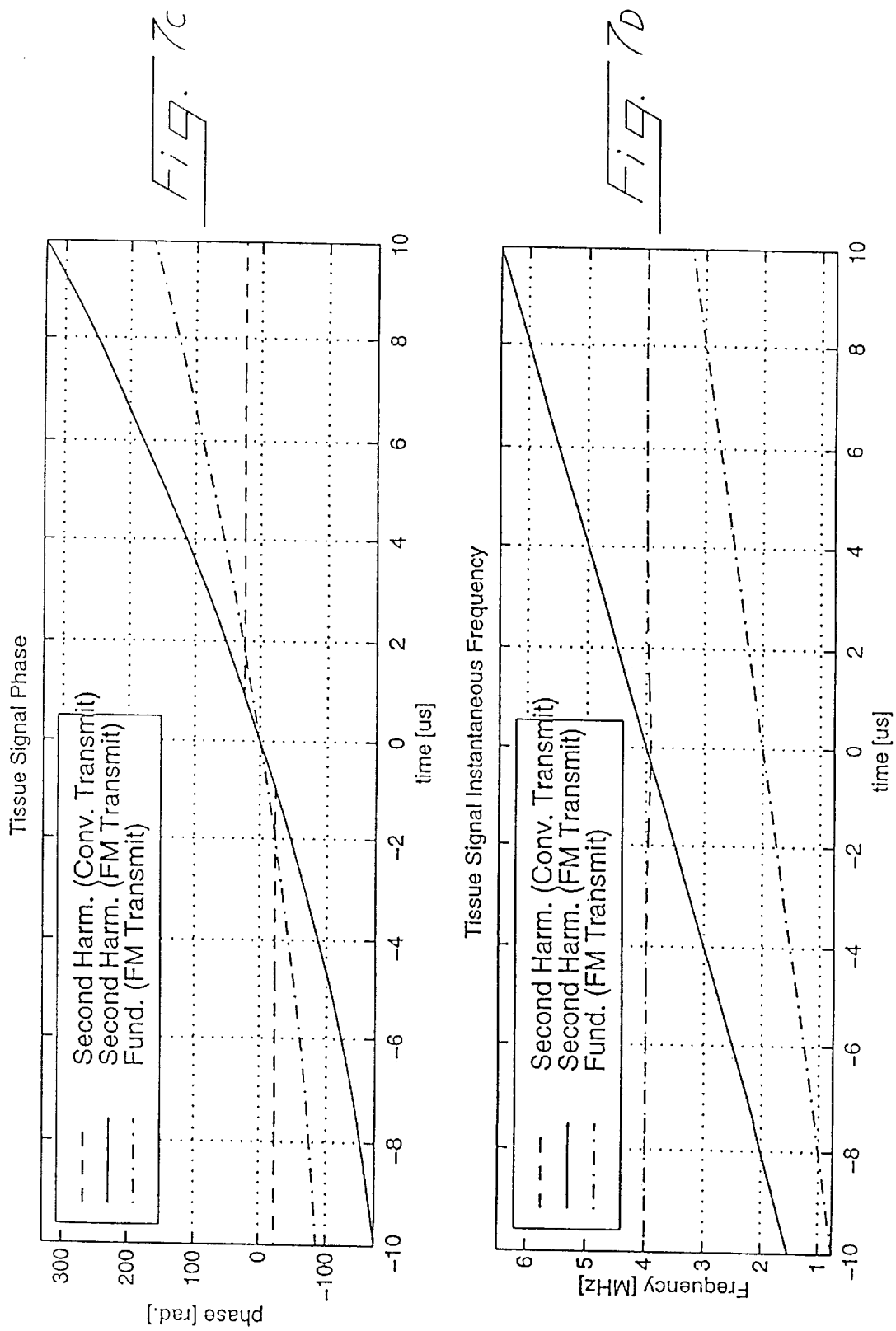

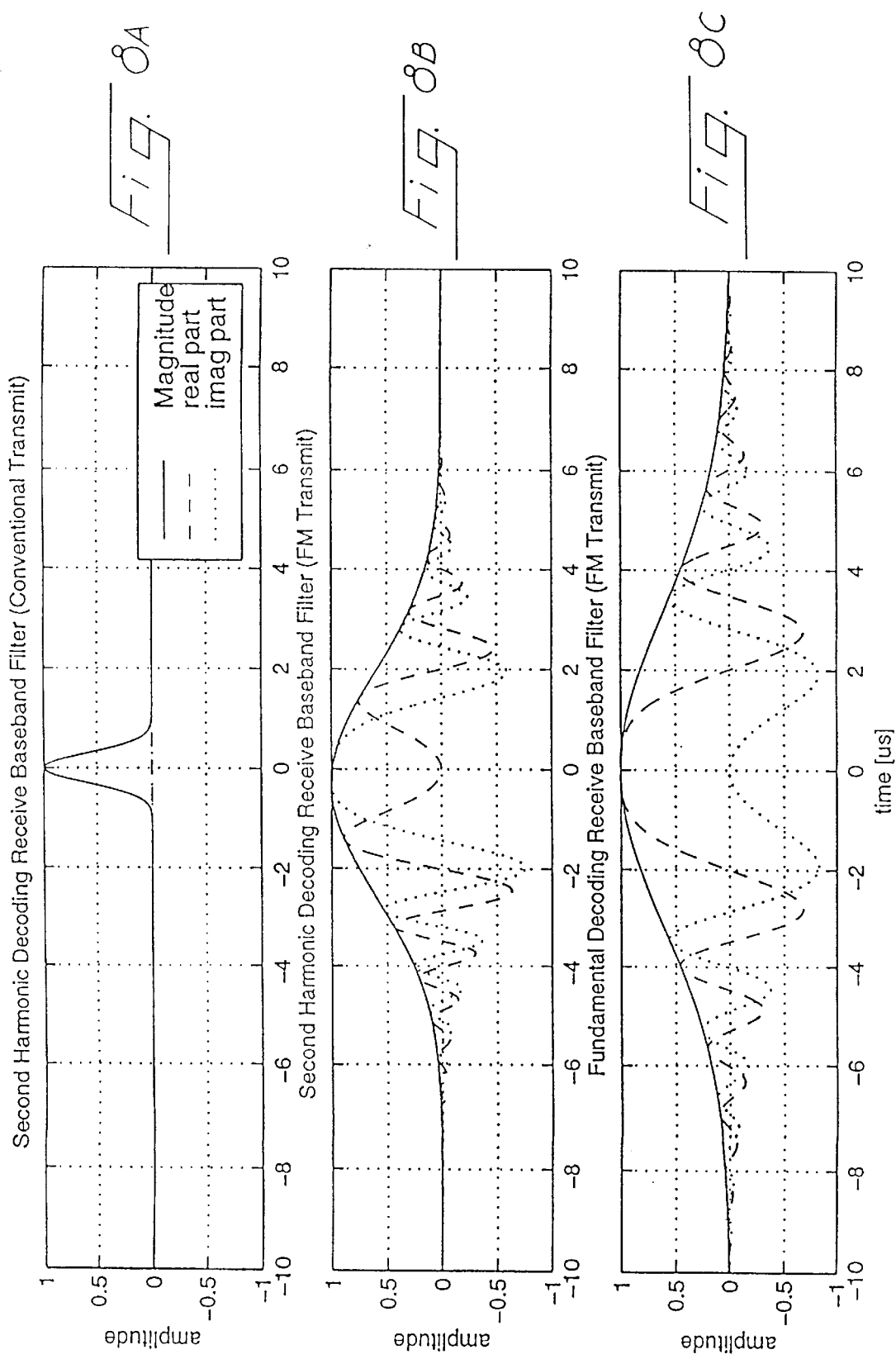

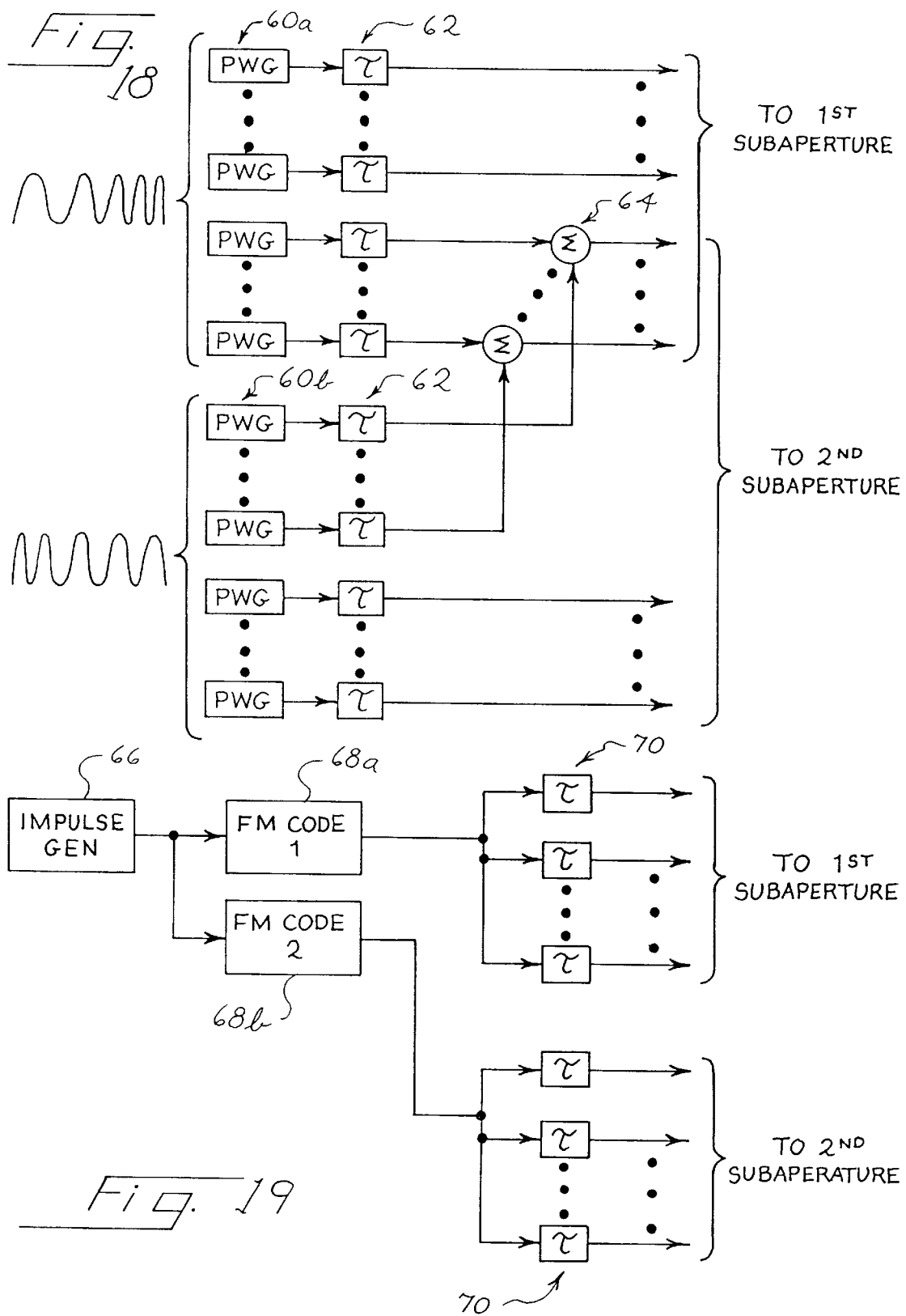

MEDICAL DIAGNOSTIC ULTRASONIC IMAGING SYSTEM USING CODED TRANSMIT PULSES

CROSS-REFERENCE TO RELATED APPLICATION

This application is related to co-pending U.S. patent application Ser. No. 09/282,510, filed Mar. 31, 1999, the entirety of which is hereby incorporated by reference.

BACKGROUND

The present invention relates to medical diagnostic ultrasonic imaging systems and methods, and in particular to such systems and methods that utilize coded transmit pulses to enhance imaging characteristics. Certain embodiments of this invention are particularly useful in motion processing imaging modes such as 2D or 3D color flow imaging, spectral Doppler imaging, tissue motion imaging, strain imaging, and pulse inversion harmonic Doppler imaging. Harmonic imaging embodiments can be used in contrast agent imaging modes as well as in tissue harmonic imaging modes. Other embodiments are particularly useful for B-mode processing.

Frequency modulated (FM) transmit pulses are known in the art for increasing average power of a signal without increasing the instantaneous peak power. This technique has been recently suggested in the medical ultrasound field for use with B-mode imaging (M. O'Donnell, Coded Excitation System for Improving the Penetration of Real-Time Phased Array Imaging Systems, IEEE Transactions on Ultrasonics, Ferroelectrics, and Frequency Control, Vol. 39, No. 3, pg. 341–351, May 1992), as well as in conjunction with contrast imaging (Y. Takeuchi, Coded Excitation for Harmonic Imaging, Ultrasonics, PH-3, 1996).

SUMMARY

The present inventor has developed improved methods for using nonlinear phase and frequency modulated coded transmission pulses in ultrasonic imaging, including in ultrasonic imaging of motion of the imaged tissue or blood, and with or without the use of contrast agents.

Certain of the embodiments described below launch first and second coded ultrasonic transmit beams into a body, timed such that the second transmit beam is launched before the first transmit beam has left the body. The first and second transmit beams of this embodiment are encoded with unique respective codes that are designed to minimize interference between echo signals from the respective transmit beams. In one form of this embodiment, the first and second transmit beams are included in a single transmit event. In other forms, the first and second transmit beams are included in separate transmit events.

In one mode, first and second ultrasonic beams are launched into a body along first and second spatially distinct transmit beam directions and used with B-mode or motion detection processing. Frame rates are improved. Multiple spectral Doppler images from independent gates are generated.

In another mode, first and second ultrasonic beams are launched into a body to focus at substantially the same point such that the two beams sample motion at different times. Unconventionally high velocity parameters are estimated and other motion parameters, including velocity parameters, may be estimated with improved accuracy.

In yet another mode, first and second ultrasonic beams are launched into a body to focus preferentially at the same point, where each beam originates from a subaperture and the receive signals are used with motion detection processing. Improved direction sensitivity to motion is obtained. The improved sensitivity may be used to estimate the vector components of velocities or used to improve the automatic placement of the direction cursor within a spectral Doppler gate.

In yet another mode, two or more coded ultrasonic beams are launched into the body with alternating polarities in a pulse inversion harmonic Doppler mode to improve the SNR while imaging contrast agents.

The following detailed description clarifies the manner in which these embodiments improve B-mode and motion detection imaging, while in many cases reducing interference problems associated with receive signals from separate transmit beams.

The invention is defined by the following claims, and this section should be taken only as a general introduction, not as a definition of the invention.

BRIEF DESCRIPTION OF THE DRAWINGS

FIGS. 2a, 2b, 2c and 2d are graphs of a conventional transmit pulse, a coded FM transmit pulse (time-bandwidth product equal to 4), transmit signal phase and transmit signal instantaneous frequency, respectively.

FIGS. 3a, 3b, 3c and 3d are graphs of a conventional tissue second harmonic signal associated with the transmit pulse of FIG. 2a, a tissue second harmonic signal associated with the transmit pulse of FIG. 2b, tissue signal phase and tissue signal instantaneous frequency, respectively. Also shown in FIGS. 3a and 3b are the envelopes of the tissue fundamental signals.

FIGS. 4a, 4b, 4c, 4d and 4e are graphs of a second harmonic decoding receive baseband filter for the receive pulse of FIG. 3a, a second harmonic decoding receive baseband filter for the receive pulse of FIG. 3b, a fundamental decoding receive baseband filter for the FM coded transmit pulse, decoding receive filter phases, and detected outputs, respectively.

FIGS. 7a, 7b, 7c and 7d correspond to FIGS. 3a through 3d, respectively, except that FIGS. 7b, 7c and 7d relate to a tissue second harmonic signal associated with the transmit pulse of FIG. 6b.

FIGS. 8a through 8e correspond to FIGS. 4a through 4e, respectively, except that FIGS. 8b through 8e relate to fundamental and harmonic echo decoding filters and signals associated with the transmit signal of FIG. 6b.

FIGS. 16, 17, 18 and 19 are schematic views of alternative architectures suitable for a coding transmitter.

DETAILED DESCRIPTION OF THE PRESENTLY PREFERRED EMBODIMENTS

The following sections will first describe in general terms selected features of the following embodiments, before turning to a theoretical analysis of the use of coded transmit beams in ultrasonic imaging and a detailed description of preferred embodiments.

General Discussion

Figure 1:
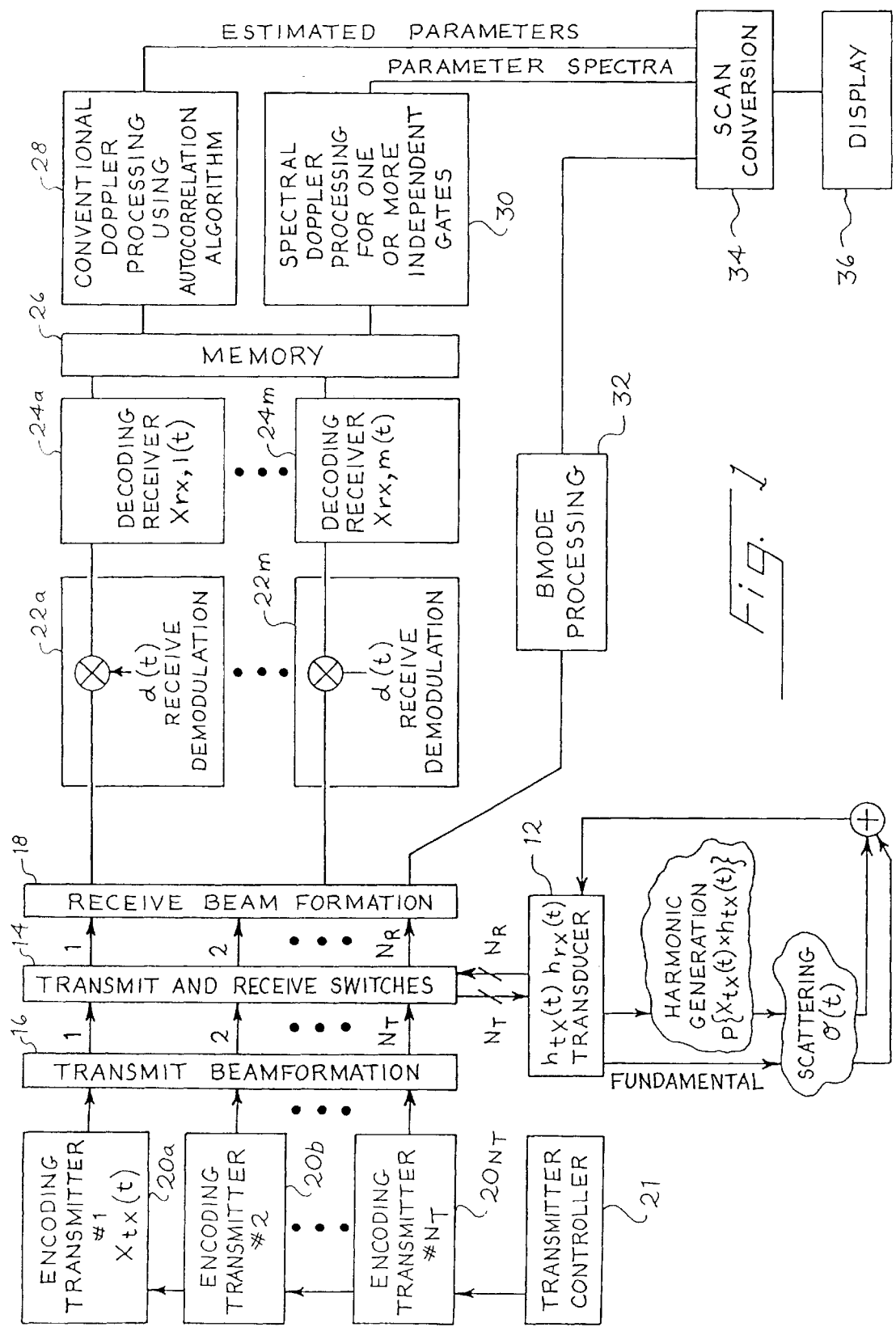
FIG. 1 is a block diagram of a medical diagnostic ultrasound imaging system that implements preferred embodiments of this invention.

As shown in FIG. 1, a transducer array 12 (which may be any suitable phased array transducer) is coupled by transmit and receive switches 14 to a transmit beamformer 16 and to a receive beamformer 18. The transmit beamformer 16 receives as input signals transmit signals from transmitters 20a, 20b, . . . 20nt. The transmit beamformer 16 applies a suitable delay profile by means of any desired combination of delays, phase changes and phase rotations and applies the coded, beamformed transmit signals to respective transducer elements of the transducer array 12. The transducer array 12 generates in response one or more transmit beams that are steered along the desired scan lines into the body being imaged.

The encoding transmitters 20a–20nt are controlled by a transmitter controller 21. The transmitter controller 21 can be programmed in several different modes of operation as appropriate for the specific embodiments described below. In one mode of operation, the transmitter controller 21 causes all of the encoding transmitters 20a–20nt to begin transmitting at the same time. In this mode of operation two or more separately coded transmit beams are formed from the same transmit event. These beams can be steered along the same or different scan lines using the same or different focus and generated by the same or different transducer elements, all as controlled by the transmit beamformer 16. In another mode of operation, the transmitter controller 21 controls all or any desired subset of the encoding transmitters 20a–20nt to create coded transmit waveforms for two separate firing events that differ in transmit code. These two separate transmit events in many applications are closely spaced such that the second transmit event is separated in time from the first transmit event by less than the time required for the first transmit event to substantially leave the body being imaged. As explained below, interference between two such closely spaced transmit beams is minimized by the use of different transmit codes on the respective transmit beams. In many applications, such separately coded transmit beams are separated by an intervening time interval that is less than the two-way propagation time for a region of interest.

As explained above, the body being imaged may include contrast agent, or alternately it may be free of added contrast agent. Typically, each coded transmit beam is characterized by a center transmit frequency that corresponds to the so-called fundamental frequency. As the beam propagates through the body, harmonic components (which may include integer or fractional harmonics) of this fundamental frequency are generated by well-known nonlinear effects. Scattering sites within the body, which may include contrast agent in some cases, scatter both fundamental energy and harmonic energy from the transmit beam back to the transducer array 12. The transducer array 12 forms echo signals in response to the scattered energy, and echo signals from individual ones of the transducer elements are beamformed by the receive beamformer 18 to form beamformed receive signals along selected scan lines. As pointed out above, one, two or more transmit beams can be included in a single firing or transmit event, and one, two or more separate receive beams can be acquired from each respective transmit beam.

The beamformed receive signals generated by the receive beamformer 18 are applied to at least two receive demodulators 22a . . . 22m. Each receive demodulator demodulates the associated receive beam to the frequency range of interest and applies the demodulated receive beam to a respective decoding receiver 24a . . . 24m. Each decoding receiver 24a . . . 24m applies a respective pulse compression function selected to correspond to the desired transmit code used by one or more of the transmitters 20a, 20b, . . . 20nt, modified as described below for the desired harmonic. The demodulated, decoded receive signals are then stored in a memory 26 until applied to image processors 28, 30. The image processor 28 can be a conventional Doppler processor that uses the well-known autocorrelation algorithm (C. Kasai, K. Namekawa, A. Koyano, and R. Omoto, Real-time two-dimensional blood flow imaging using an autocorrelation technique, IEEE Trans. Son. Ultrason., Vol. SU-32, pp. 458–464, 1985) to generate estimated motion parameters such as Doppler velocity, Doppler energy, Doppler variance, and combinations thereof. The image processor 30 can be a conventional spectral Doppler image processor that uses the well-known Fast Fourier Transform (FFT) algorithm to generate spectral parameter spectra for one or more independent range gates.

The system of FIG. 1 further includes a B-mode processor 32 that responds to beamformed receive beams from the receive beamformer 18 and applies B-mode image signals to the scan converter 34. The B-mode processor 32 includes receive demodulators and decoding receivers that are characterized by pulse compression functions similar to those of the decoding receivers 24a . . . 24m.

The scan converter 34 generates images for presentation on a display 36. These images can include any desired combination of a B-mode images from the B-mode processor 32, estimated motion parameters from the Doppler processor 28, and Doppler parameter spectra from the spectral Doppler processor 30.

The system of FIG. 1 can be used for fundamental imaging modes and/or harmonic imaging modes, with or without added contrast agent, depending upon the specific application. The harmonic imaging modes may image fractional harmonics, such as subharmonics and ultraharmonics.

For applications that may be electrically-limited or MI-limited, but not limited by thermal constraints, spatial-peak-temporal-average limits, or otherwise, the ultrasonic signal transmitted by the transducer 12 is preferably encoded and also lengthened (uncompressed or expanded) to increase the total energy. Later in the signal processing chain, the received signal is decoded and re-compressed to maximize axial detail resolution. This method effectively increases the time-bandwidth product by increasing the temporal duration of the transmitted signal while maintaining the over-all bandwidth (which is proportional to the axial detail resolution). The technique of coded transmission with decoding receive filtering can be combined with conventional motion detection techniques as described below to improve SNR, frame rates, directional sensitivity, contrast agent specificity, and/or parameter estimation accuracy. Further, these techniques may be used with B-mode imaging to improve frame rates.

The system of FIG. 1 can be used to implement each of the seven methods described below, using either fundamental or harmonic imaging modes with or without the use of contrast agents.

1. The combination of pulse-compression techniques with motion detection:

The pulse-compression techniques described below may be used to improve the SNR when detecting motion in a target by insonifying the target with two or more temporally expanded pulses steered in the same direction, and then processing the resulting echo signals to estimate motion parameters.

2. The use of two or more simultaneously transmitted coded transmit beams with motion detection processing or B-mode processing:

Two or more coded transmit beams may be transmitted simultaneously to increase frame rates in two dimensional (2D) or three dimensional (3D) motion imaging, 2D or 3D B-mode imaging, or to make available two or more independent spectral Doppler gates without loss in temporal resolution. Each transmit delay profile corresponding to a selected focus is associated with a unique nonlinear phase modulation function, and a respective decoding receive filter for each unique profile is used to maintain adequate acoustic isolation between two or more spatially distinct ultrasound lines or two or more spatially distinct foci. With the ability to transmit the superimposed multiple transmit beams simultaneously, fewer transmit firings are necessary to generate an image frame, thereby increasing frame rates in fundamental and harmonic imaging, both with and without contrast agents. Multiple receive beams may also be acquired from each transmit beam. In spectral Doppler, two or more gates may be placed independently in different directions and at different ranges without reducing temporal resolution or significantly degrading the spectra-vs.-time waveforms.

3. The use of subaperture encoding:

Two or more subapertures within an active transducer aperture may be uniquely encoded and decoded to improve sensitivity to non-axial motion for multidimensional motion imaging and to improve the automatic placement of a spectral Doppler cursor. For example, when a transducer aperture is divided into two separately coded subapertures on opposite sides of the center of the array, the direction with the greatest sensitivity to motion will no longer be perpendicular to the face of the transducer at the center of the active aperture. The direction of greatest sensitivity for each sub-aperture will be away from this perpendicular and defined about the center of the paired transmit and receive subapertures. This improves the ability of motion detection processing to detect motion that is parallel to the face of the active aperture, since changes between two or more pulses will be larger and more likely above the level of detectability due to the higher spatial frequencies in the lateral dimension. Also, the use of two or more subapertures allows the estimation of the direction of motion within a spectral Doppler gate. Improved automatic placement of a spectral Doppler direction cursor is possible due to the improved sensitivity to the lateral component of the estimated direction. Two or more subapertures may be defined within a 1 D array or a multidimensional array. This approach can be applied to 2D or 3D color motion imaging, spectral Doppler processing, or other motion detection methods.

4. The use of interpulse encoding with spectral Doppler processing:

Pulse-specific encoding in conventional spectral Doppler processing for a single pre-selected gate may be used to provide more accurate high velocity detection with reduced range-velocity ambiguity or to reduce estimation inaccuracies. To avoid strong returns from areas other than a selected gate, the pulse repetition interval (PRI) is typically set based upon the location of the gate from the transducer. This interval fixes the maximum detectable velocities. If pulses are fired at a rate greater than 1/PRI, extra samples may be acquired between the original pulses. These extra pulses may be used to improve accuracy by averaging methods, or the higher sampling rate can yield greater maximum detected velocities. However, motion from areas other than the gate of interest can introduce inaccuracies in the displayed parameters-vs.-time waveform. These inaccuracies may exist if returns from other locations arrive at the transducer at the same time as the returns from the gate of interest. These inaccuracies can be reduced if a unique coded waveform is assigned to each of the transmitted pulses. This approach can be applied in fundamental and harmonic spectral Doppler imaging.

5. The use of interpulse encoding with multi-dimensional motion processing:

Pulse-specific encoding in 2D color motion mapping of tissue, blood, or contrast agent, which uses the conventional autocorrelation algorithm for motion estimation, may be used to increase parameter estimation accuracy, improve frame rates, and/or increase velocity dynamic ranges.

For each spatial location within a 2D color motion map in a conventional system, motion parameters are estimated based upon a fixed number of samples, the flow sample count (FSC), as determined by FSC transmitted pulses. The time interval between these samples or pulses, the PRI, is chosen based on the velocities of interest. For high velocity flow, minimum PRI's are chosen such that returns from other locations do not strongly interfere with the estimation of motion. Additional pulses, beyond the FSC, may be transmitted without significantly interfering with the original pulses by encoding the additional pulses with codes that are different from the codes associated with the original pulses. The additional pulses can be transmitted in between the original pulses without any loss in frame rate. The additional pulses can be used as an additional set of data, providing additional information, to improve estimation accuracy, improve frame rates, and/or increase maximum detectable velocities.

This method effectively acquires and processes FSC samples in less time. For frame rates similar to the conventional technique the additional pulses may be used to improve estimation accuracy; alternatively, the frame rate can be increased by transmitting the additional encoded pulses between the original pulses until FSC samples are acquired. Since this alternative method effectively increases the firing rate, improved frame rates are possible with estimation accuracy similar to the conventional methods. The increased firing rate with the additional pulses can also be used to increase the maximum detectable velocities. Since the PRI is effectively decreased, higher velocities and therefore greater dynamic ranges are detectable before aliasing is introduced.

6. The use of pulse-compression techniques and/or interpulse encoding with pulse inversion harmonic Doppler imaging:

Pulse inversion harmonic Doppler is a technique where a conventional Doppler transmit pulse sequence composed of FSC pulses is modified by alternating the polarities of the transmitted pulses while preferably imaging contrast agents. This technique has been described in Hwang U.S. Pat. No. 5,706,819 and may increase detection specificity of second harmonic energy. The pulse inversion harmonic Doppler technique relies upon transmitting two or more pulses with alternating envelope phases (i.e. 0, 180, 0, etc.) that have overlapping fundamental and second harmonic radio frequency spectra and then processing the ensemble of FSC pulses with conventional Doppler processing. Modified clutter/wall filters are used to combine the pulses. With this modified insonification technique, fundamental signal returns are modulated by half the pulse repetition frequency (PRF=1/PRI) in the Doppler domain, while the second harmonic signal returns remain intact (i.e., unmodulated). This separation of second harmonic and fundamental signals in the Doppler domain, provided half the conventional aliasing limit is not violated, allows shorter transmit pulses to be transmitted and received than is conventionally used for harmonic imaging, while the two Doppler spectra are maintained in fixed known frequency bands. This provides increased second harmonic axial resolution and therefore finer spatial sampling of flow. Less corruption of desired flow signals with fundamental and harmonic clutter is a benefit from the finer spatial sampling.

Because of the finer spatial sampling and ability to preferentially filter the fundamental Doppler signals, the pulse inversion harmonic Doppler technique has the potential to increase agent specificity, in particular, for small vessels. However, at high pulse amplitudes agent disruption reduces the ability of the technique to accurately separate the harmonic and fundamental Doppler spectra. Thus, conventional Doppler techniques that exploit reduced correlations between pulses due to agent disruption may perform similarly. At low pulse amplitudes where agent disruption is less significant, the pulse inversion harmonic Doppler technique can improve agent specificity compared to other available techniques since harmonic and fundamental spectra can be more accurately separated. However, to avoid significant agent disruption peak pressure levels are kept low, thereby reducing the SNR. Pulse-compression techniques can increase the SNR and improve image quality. Further, interpulse encoding techniques can be used to relax the unconventional maximum velocity detection limit imposed by the pulse inversion harmonic Doppler technique. Instead of the maximum detection limit being half the conventional velocity limit, the limit can be increased back to the conventional limit and beyond the conventional limit. Further, interpulse encoding can be used to average additional parameter estimates and improve parameter estimation accuracy.

7. The combination of any desired subset or fullset of the methods described in paragraphs 1–6 above.

Mathematical Description of Pulse Coding and Decoding

Improvements in the SNR are possible by combining the well-known encoding and decoding techniques for fundamental imaging with conventional motion detection techniques. In addition, harmonic decoding for harmonic imaging is developed here and can also be combined with conventional motion detection techniques and B-mode processing techniques.

As discussed above in conjunction with FIG. 1, one or more (up to m) decoding receivers may be used depending on the chosen implementation. Any of the methods presented below may use two or more unique receive filter impulse responses, but if the data rate is sufficient a single receiver may be used.

The following mathematical description, which ignores the contribution from tissue attenuation, acoustic diffraction, and the beam formation process, applies to the system of FIG. 1. The formation of an ultrasound line can be modeled as:

$$I(t)=[P\{X_{tx}(t)*h(t)\}*\theta(t)*h_{rx}(t)]d(t)*X_{rx}(t) \tag{1}$$

where $X_{tx}(t)$=transmit waveform $h_{tx}(t)$=transducer voltage-to-pressure transfer function $P\{\ldots\}$=operator p models harmonic signal generation $\theta(t)$=scatterer response $h_{rx}(t)$=transducer pressure-to-voltage transfer function $d(t)$=demodulation function $X_{rx}(t)$=receive filter or pulse-compression decoding filter t=time

*=convolution operation

To increase the transmit energy without sacrificing axial detail resolution, the conventional transmit waveform $X_{tx}(t)$ with amplitude modulation a(t) and modulation frequency $f_m$ can be expressed as follows:

$$X_{tx}(t)=Re\{a(t)e^{j2\pi f_m t}\}. \tag{2}$$

$X_{tx}(t)$ can be modified with a temporally dependent phase term $\phi(t)$. Note, "Re" stands for the real part of $\{\ldots\}$. In general, the new transmit waveform is $$X'_{tx}(t)=Re\{a(t)e^{j\phi(t)}e^{j2\pi f_m t}\}, \tag{3}$$

where $$\phi(t)=K_1 t^2+K_2 t^3+\ldots+K_n t^{(n+1)} \tag{4}$$

and $K_i$ are arbitrary constants. Proper selection of $\phi(t)$ and a(t) allows a compact fixed-bandwidth temporal pulse with a time-bandwidth product of about one to be temporally expanded to greater time-bandwidth products allowing greater transmitted signal energy. After receiving scattered signals from tissue, a properly designed receiver can compress the temporally expanded pulse and restore a compact pulse. This process retains the preferred axial detail resolution associated with the specified bandwidth without significant degradation from the expanded transmit pulse. Excellent axial detail resolution is only maintained with the proper decoding receiver and adequate rejection of out-of-band frequency components. With proper decoding with a receiver designed to selectively listen for desired second, lower order, or higher order harmonic energy, the time-bandwidth product can be increased beyond the conventional value of about one, improving the SNR. As is well known in the art, a preferred decoder for fundamental imaging that may maximize SNR is a matched filter. Thus, after demodulation at the dominant fundamental frequency, the receiver decoder can be a scaled version of the time-reversed phase-conjugate of $a(t)e^{j\phi(t)}$.

For harmonic imaging, the preferred decoder is dependent on the order and mechanism of the harmonic signal generation. Again, a matched filter, matched to the harmonic of interest, is a preferred decoder. For second harmonic tissue imaging a reasonable model can be obtained by solving the well-known Riemann wave equation (*Nonlinear Acoustics*, Mark F. Hamilton, et al. ed, 1998, pg 75).

$$\frac{\partial g}{\partial t} + \frac{C_o \partial g}{\partial z} = \left(\frac{Bg}{\rho_o C_o^2}\right)\frac{\partial g}{\partial t} \text{ for the pressure } g(t,z), \quad (5)$$

where

Co is the small signal sound speed $\rho_o$ is the ambient density

B is the parameter of nonlinearity, by applying the boundary condition, or forcing function, equal to the transducer's transmit pressure signal at its face; i.e., $$g(t,z)\Big|_{z=0} = f(t).$$

See, for example: page 75 of *Nonlinear Acoustics*, edited by Mark F. Hamilton and David T. Blackstock, copyright 1998.

Using straight-forward perturbation analysis (see for example: age 281, section 2 of *Nonlinear Acoutics*) the general model takes the form $$g(t,z) = f(t-z/Co) + Kt\frac{d[f^2(t-z/Co)]}{dt}, \quad (7)$$

which yields a second harmonic signal generated from the temporal derivative of the squared fundamental pressure signal, f(t), with Kt equal to the tissue material properties. An example of a model that may be applicable for contrast agent imaging of second harmonic energy excludes the temporal derivative, but is still dependent on the square of the fundamental pressure.

Using the general transmit waveform signal in eq. (3), the model operation p{ . . . }, and assuming the transducer's transmit transfer function has insignificant influence over the frequency band of interest, the generated second harmonic signal in tissue can be shown to be $$X_{2nd}(t) = D_i \text{Re}\{n(t)e^{j4\pi f_m t}\} + a(t)\frac{d[a(t)]}{dt}, \quad (8)$$

where $$n(t) = b(t)a^2(t)\left[2\pi f_m + \frac{d[\phi(t)]}{dt}\right]e^{j2\phi(t)}e^{j\theta(t)} \quad (9)$$

$$b(t) = \left[\frac{\left(\frac{d[a(t)]}{dt}\right)^2}{a^2(t)\left(2\pi f_m + \frac{d[\phi(t)]}{dt}\right)^2} + 1\right]^{1/2} \quad (10)$$

$$\theta(t) = \tan^{-1}\left\{\frac{a(t)\left(2\pi f_m + \frac{d[\phi(t)]}{dt}\right)}{d\frac{[a(t)]}{dt}}\right\} \quad (11)$$

Di=constant

Notice that the second harmonic signal has been effectively frequency modulated up by twice the original modulation frequency of $f_m$, i.e., $e^{j4\pi f_m t}$, and there is additional low frequency energy near DC due to the last term $$a(t)\frac{d[a(t)]}{dt}.$$

This last term appears because during nonlinear acoustic propagation signal peaks travel faster than signal troughs for a finite bandwidth signal; i.e., positive relative pressure (peaks) produce greater tissue sound velocities than negative relative pressure (troughs). For second harmonic imaging of contrast agents, $$n(t)=a^2(t)e^{j2\pi(t)} \quad (12)$$

After receiving the scattered tissue energy and appropriate per channel delay, phasing, and apodization are applied by a beamformer, the harmonic signals of interest can be demodulated to a desired frequency band for further processing. A preferred band is baseband. If the demodulation function d(t) is chosen centered at the second harmonic frequency, i.e., $$d(t)=e^{j2(2\pi f_m t)} \quad (13)$$

and $X_{rx}(t)$ is chosen to be equal to $Y^*_{2nd}(-t)$ where $$Y_{2nd}(t) = b(t)a^2(t)\left[2\pi f_m + \frac{d[\phi(t)]}{dt}\right]e^{j2\phi(t)}e^{j\theta(t)} \quad (14)$$

for tissue second harmonic energy, or $$Y_{2nd}(t)=a^2(t)e^{j2\phi(t)} \quad (15)$$

for contrast agent second harmonic energy, and * is the complex conjugate operation, then a preferred embodiment that maximizes the SNR and maintains excellent axial detail resolution can be realized. In this preferred embodiment, a matched filter, which may maximize the SNR, is used for the pulse-compression receiver $X_{rx}(t)$. A conventional receiver would lack the decoding and additional nonlinear phase modulation necessary to restore the desired axial resolution. After demodulation, the preferred pulse-compression matched receiver is a time-reversed phase-conjugate of $$n(t) \quad (16)$$

where the demodulation signal processing step effectively shifts the frequency band to a preferred frequency band. The matched filter, or more generally the pulse compression filter, can effectively suppress the low frequency term near DC and the fundamental energy or other undesired energies. Amplitude modulation in the receiver other than a matched filter envelope may also be used if desired. In particular, additional pulse shaping may be used to help suppress unwanted range lobes.

EXAMPLE

The following is an example of a nonlinear quadratic phase modulated (PM), linear frequency modulated (FM) chirp pulse-compression code for second harmonic tissue imaging. The transmit signal has the following characteristics:

1) The amplitude is modulated with a Gaussian envelope of temporal duration:

$$T=(\alpha)^{-1/2}; \quad (17)$$

where the duration is defined by the −6.82 dB amplitude below the peak;

2) The frequency bandwidth at the −6.82 dB level below the peak is $$W = \left(\frac{\alpha^2 + \gamma^2}{\alpha}\right)^{1/2}; \quad (18)$$

3) The time-bandwidth product is defined as:

$$TW = \left(1 + \left(\frac{\gamma}{\alpha}\right)^2\right)^{1/2}. \quad (19)$$

The general transmit signal is $$X'_{tx} = Re\{e^{-\pi\alpha t^2} e^{j\pi\gamma t^2} e^{j2\pi f_m t}\}, \quad (20)$$

and for a specified bandwidth W (i.e. axial detail resolution) and desired pulse duration T, the instantaneous frequency in radians per second is $$\hat{\omega} = 2\pi(\gamma t + f_m) \quad (21)$$

Using eq. (13) above for this example, the receive pulse-compression matched filter after demodulation at the second harmonic frequency is $$X_{rx}(t) = \quad (22)$$

$$D_2\left[\frac{\alpha^2 t^2}{(f_m - \gamma t)^2} + 1\right]^{1/2} |f_m - \gamma t| e^{-2\pi\alpha t^2} e^{-j2\pi\gamma t^2} e^{j\tan^{-1}[(f_m - \gamma t)/\alpha t]},$$

where $D_2$ is a constant. A reasonable approximation for typical time-bandwidth products that can be obtained with current medical ultrasound systems is $$X_{rx}(t) = jD_3 e^{-2\pi\alpha t^2} e^{-j2\pi\gamma t^2}, \quad (23)$$

where $D_3$ is a constant. Note, the time-bandwidth product for a clinical system will likely be determined by Ispta limits, thermal limits, and per channel electrical power. FIGS. 2 through 9 are examples of the signals at different stages in a system implementation. FIGS. 2 through 5 are representative of a system with a time-bandwidth product of 4, while FIGS. 6 through 9 are representative of a system with a time-bandwidth product of 8; i.e., the transmit signal temporal length used to produce the latter four figures was twice the transmit signal length used to produce the former four figures. The transmitted bandwidth for the two sets of four figures were identical. In general, systems with time-bandwidth products less than 50, more preferably less than 20, and most preferably less than 10 are preferred.

Description of FIGS. 2 Through 9:

In the examples of FIGS. 2–9, the transmit modulation frequency is 2 MHz and the frequency bandwidth is 1 MHz. FIGS. 2a and 6a show a conventional transmitted signal, and the corresponding transmit envelope, in each figure without a time-dependent, nonlinear phase modulation; these two conventional transmit signals are identical and are shown in each case as a reference. FIGS. 2b and 6b each show a quadratic PM or linear FM coded transmit signal, and the corresponding transmit envelope. The peak signal levels are identical in all four figures, as would be typical based on electrical limits or desired spatial peak acoustic limits. FIGS. 2c and 6c show the linear transmit phases for the conventional and nonlinear phases for the coded signals, as shown in the preceding figures. FIGS. 2d and 6d show the instantaneous frequencies corresponding to the transmit phases as determined by the temporal derivative of these phases. Notice that the coded transmit signal phases are distinctly different from the conventional transmit signal phases and are nonlinear.

Figures 3C, 3D:
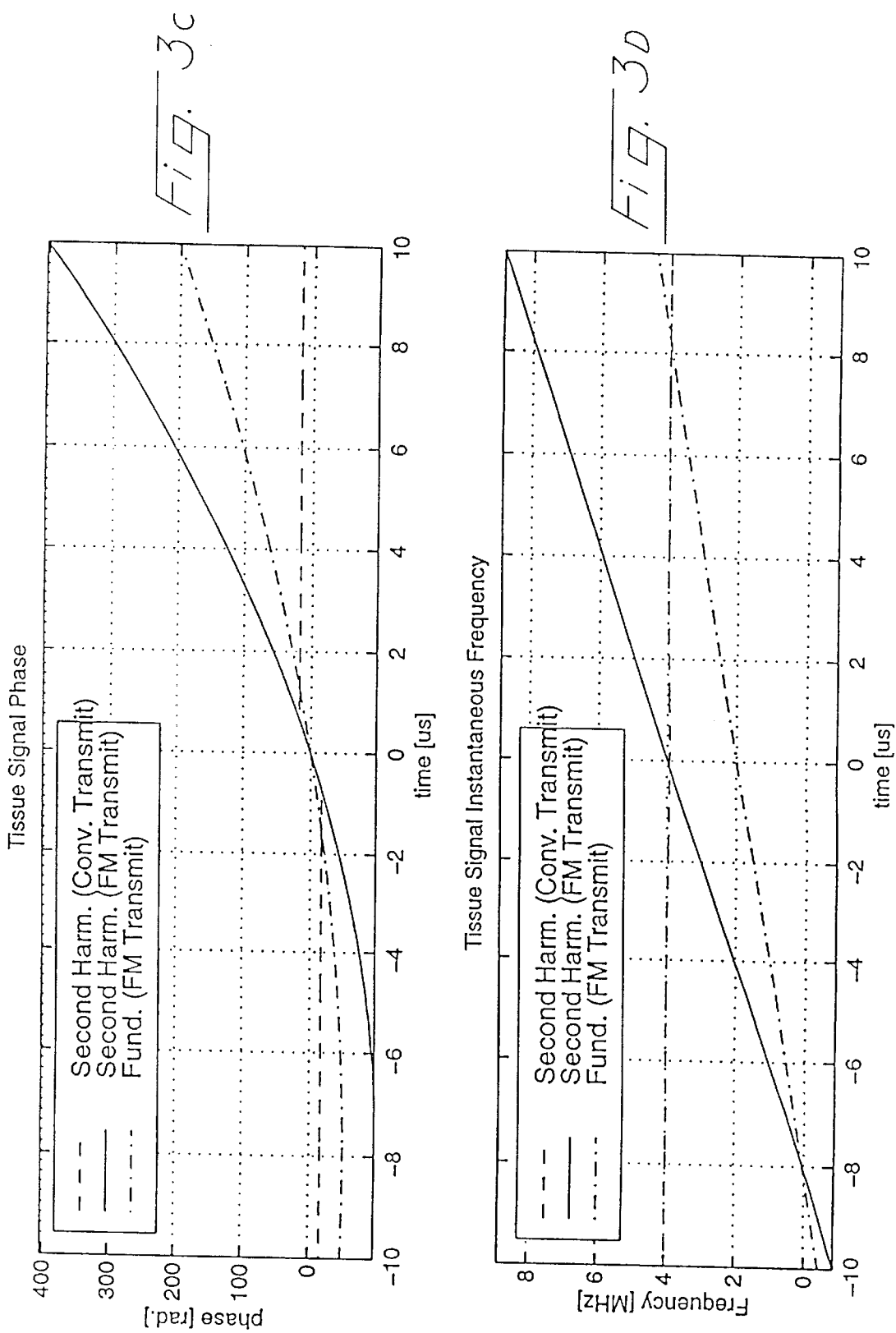
Figure 4D:
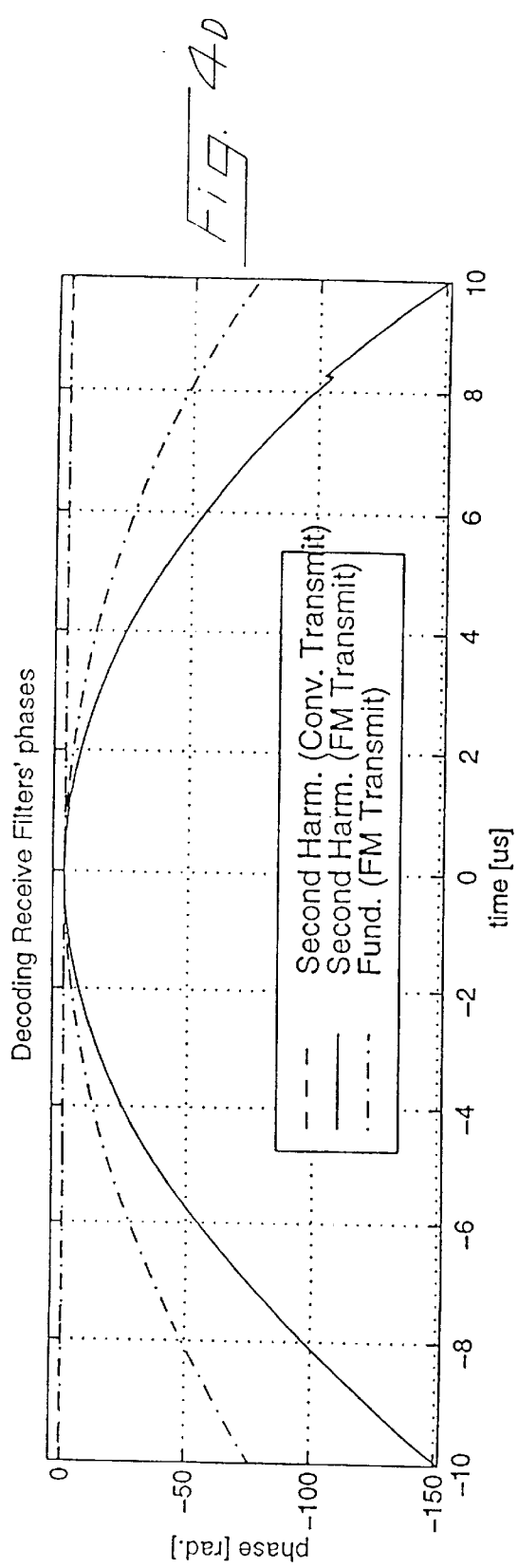
Figure 4E:
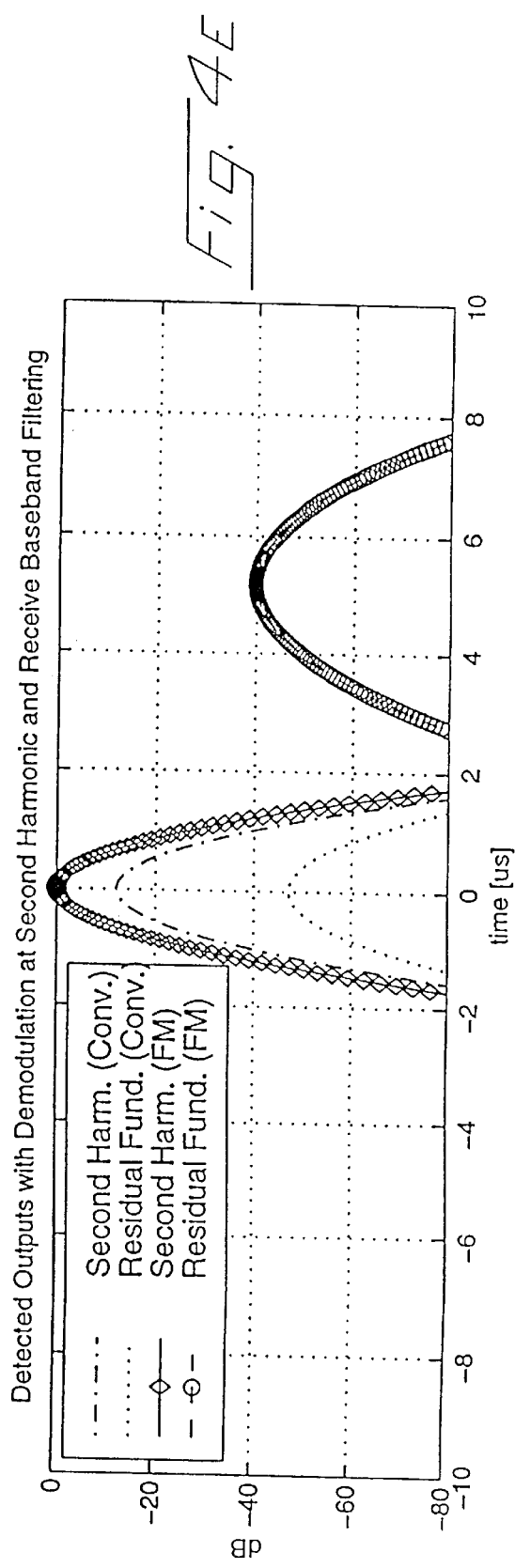
Figures 8D, 8E:
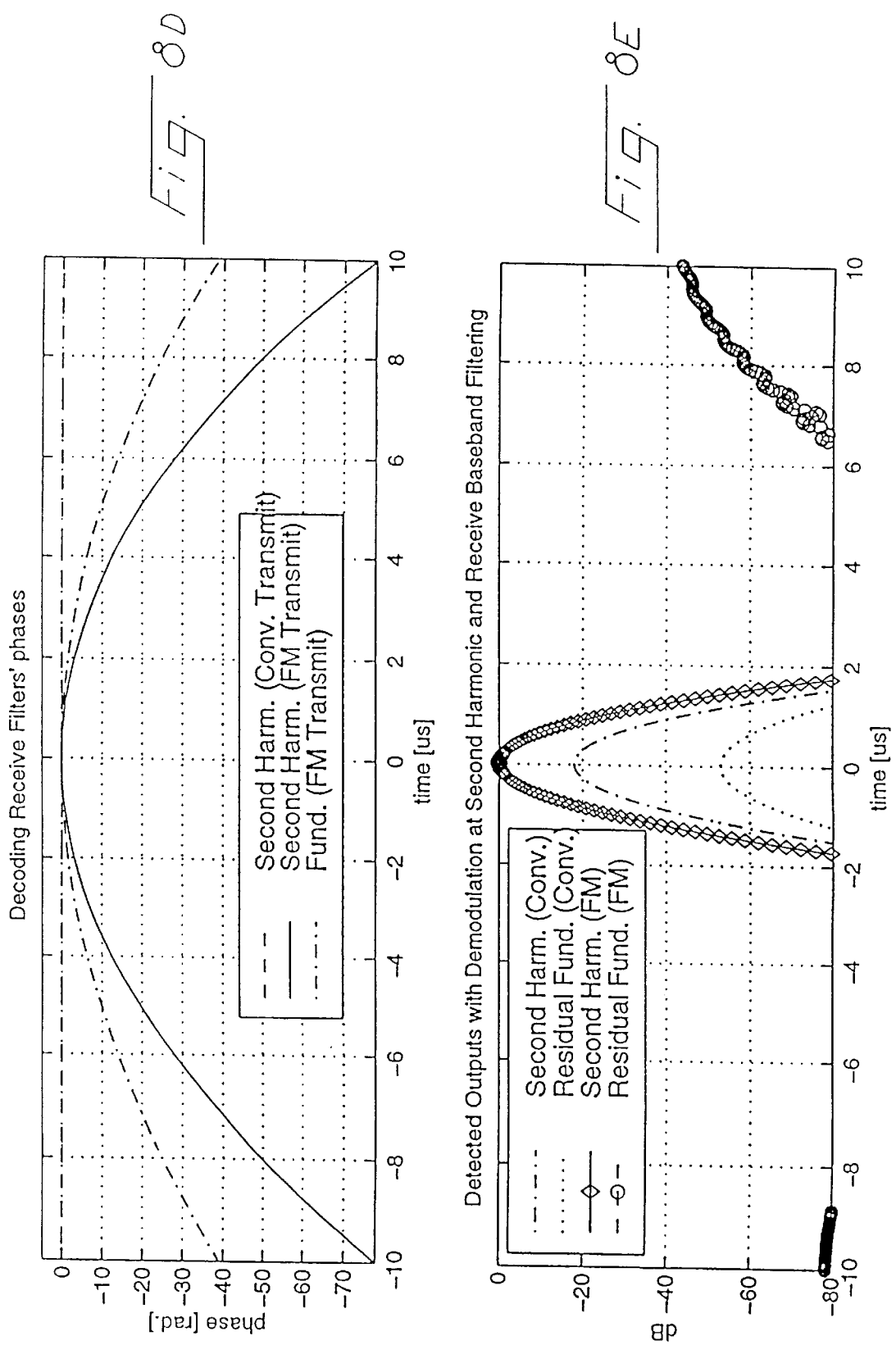

FIGS. 3a and 7a show the tissue second harmonic signal and its envelope associated with the conventional transmit signal where tissue attenuation and acoustic diffraction have been excluded. Also the tissue fundamental signal envelopes are shown for reference in these figures. Notice that the second harmonic signal provides improved axial detail resolution. FIGS. 3b and 7b show the tissue second harmonic signal and its envelope associated with the respective coded transmit signal. Again, these figures show the tissue fundamental signal envelopes for reference. FIGS. 3c and 7c show the tissue signal phases for the second harmonic signal with the conventional transmit signal, the second harmonic signal with the coded transmit signal, and the fundamental signal with the coded transmit signal. FIGS. 3d and 7d show the instantaneous frequencies corresponding to these tissue signal phases. Notice that the tissue signal phases and instantaneous frequencies for each type of tissue signal and each type of transmit signal are unique. It is necessary to take these differences into account when designing an optimized pulse-compression (or decoding) receive filter. In particular, the phase varies twice as fast as a function of time for the tissue second harmonic signal as compared to the tissue fundamental signal when coded transmit signals are launched from the transducer. FIGS. (4a, 4b, 4c) and (8a, 8b, 8c) show the pulse-compression, or decoding, receive baseband filter components for filtering second harmonic and fundamental received signals. In each of the two sets, the three figures show the second harmonic decoding filter with a conventional transmit signal, the second harmonic decoding filter with a coded transmit signal, and the fundamental decoding filter with a coded transmit signal, respectively. The latter of each set of three figures is provided for comparison and would be typical for imaging tissue with fundamental signals. Each figure shows the real part, the imaginary part, and the magnitude of each filter's response. Notice that the receive decoding filter for the second harmonic signal is different from the receive decoding filter for the fundamental signal when coded transmit signals are launched from the transducer. These differences are also seen by plotting the phase of the receive filter as a function of time. FIGS. 4d and 8d show these phases for the three different types of filters. Note that the phases change twice as fast as a function of time for the second harmonic as compared to the fundamental when coded transmit signals are employed. For imaging of higher or lower order harmonics the instantaneous phase of the decoding filter preferably matches the desired harmonic phase changes. For example, a subharmonic of order ½ would be preferentially decoded with a filter whose phase changes at half the rate as the transmitted signal's phase. FIGS. 4e and 8e show the final output signals after proper demodulation at the dominant second harmonic frequency (4 MHz), baseband receive filtering with a second harmonic pulse-compression filter (from Figures 4a or 4b and FIGS. 8a or 8b, respectively, for the two cases), and display detection. Notice the following:

1) The axial resolutions, as defined by the width of the output signals, for the two second harmonic signal processing techniques are identical. With coded transmit signals and proper receive filtering the axial detail resolution is maintained.

2) The energy in the second harmonic returned signal associated with the coded pulse-compression technique is greater than the returned energy associated with the conventional, non-coded, technique. Additional energy was made available by the temporally expanded transmit waveforms. Notice that the difference in returned detected signal energy between the two separate cases (case 1 with time-bandwidth product=4 and case 2 with time-bandwidth product =8) is greater for the larger time-bandwidth product of 8, as expected.

3) There exists a residual fundamental signal for both signal processing techniques, coded and non-coded, due to imperfect suppression of fundamental energy. The coded signal processing technique effectively shifts in time the dominant residual energy with respect to the conventional, non-coded, signal processing technique. This residual energy will be insignificant in a clinical setting for appropriately selected signal bandwidths. Larger bandwidths will generate less fundamental suppression due to frequency spectral overlap.

Poor fundamental energy suppression or unacceptable residual fundamental energy can further be reduced with proper analytic filtering of FSC received pulses associated with alternating transmitted envelope phases or polarities. This filtering is typically implemented as a clutter or wall filter, well-known to those skilled in the art. The filtering of multiple FSC received pulses of an ensemble can effectively accentuate the desired harmonics of interest while attenuating undesired fundamental or other odd harmonic energy. For example, two pulses transmitted with opposite phases (i.e., 0 and 180 degrees) in the same direction can be added with a [1 1] clutter filter impulse response after the pulse-compression receive filter. This effectively suppresses fundamental signals while at the same time increasing the usable axial detail resolution and SNR of the second harmonic signals. The use of a clutter filter for filtering purposes is well known for motion detection imaging. The use of a clutter filter with a [1 1] impulse response for B-mode imaging is equivalent to a simple summation of two pulses. Therefore, this technique for suppressing fundamental energy applies to B-mode and motion detection imaging for two or more acquired pulses. In FIGS. 4e and 8e these multiple pulse combinations would reduce the residual fundamental signal energy.

Figure 5:
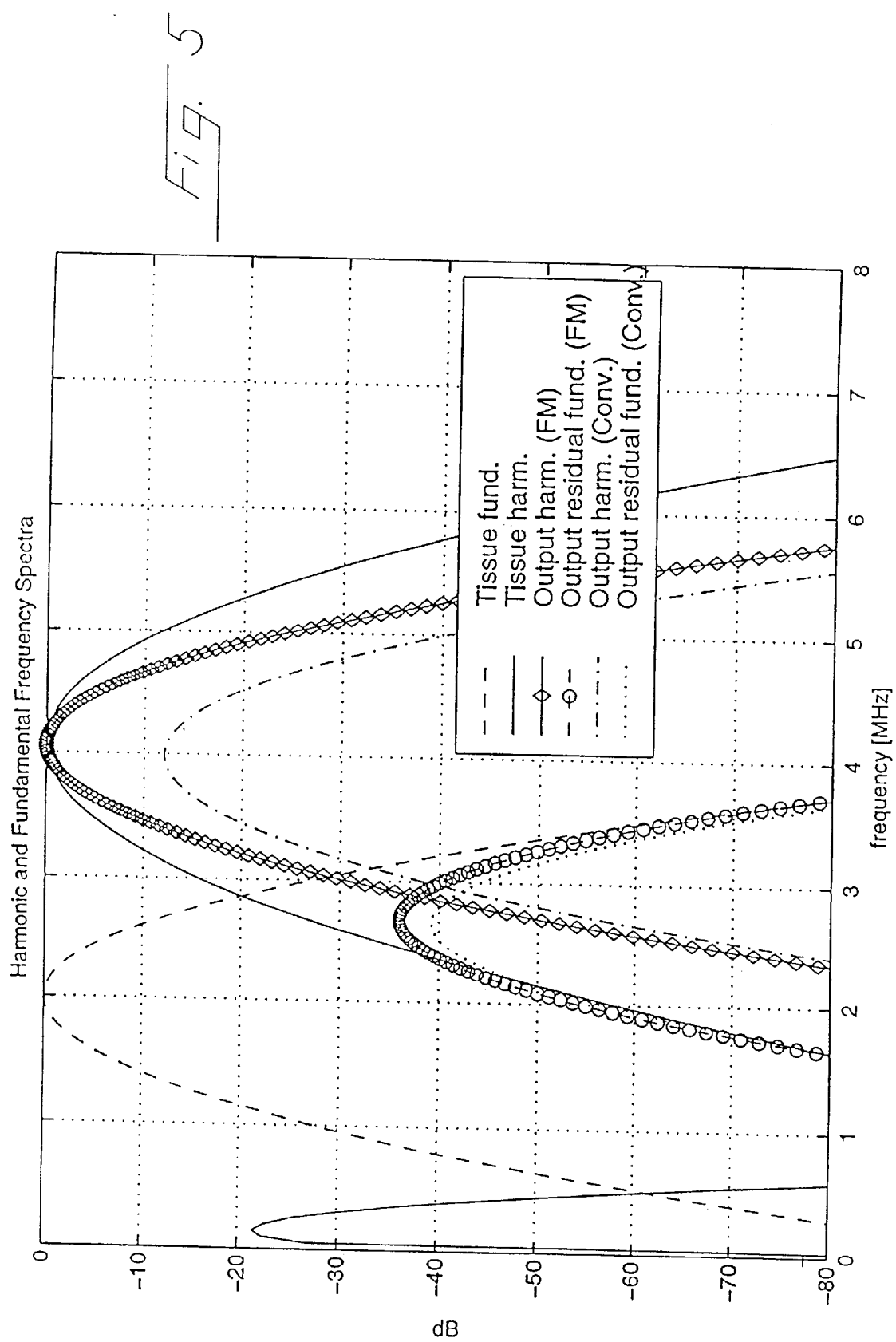
FIG. 5 is a graph of harmonic and fundamental frequency spectra.
Figure 6A:
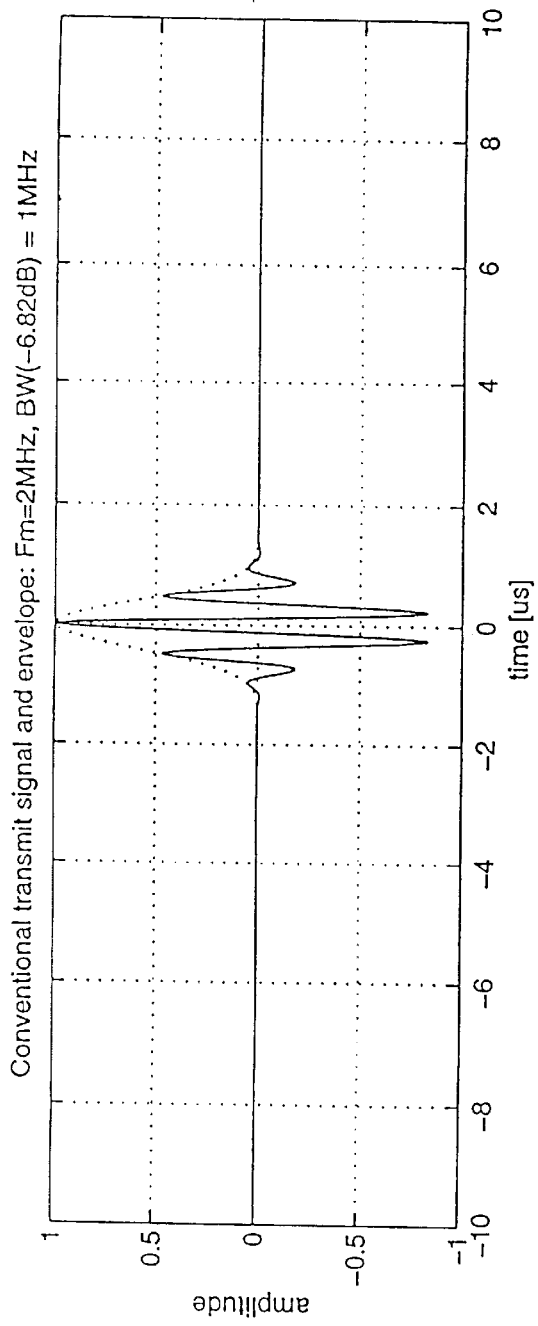
FIGS. 6a through 6d correspond to FIGS. 2a through 2d, respectively, except that FIGS. 6b, 6c and 6d relate to a coded transmit signal having a time-bandwidth product of 8.
Figure 6B:
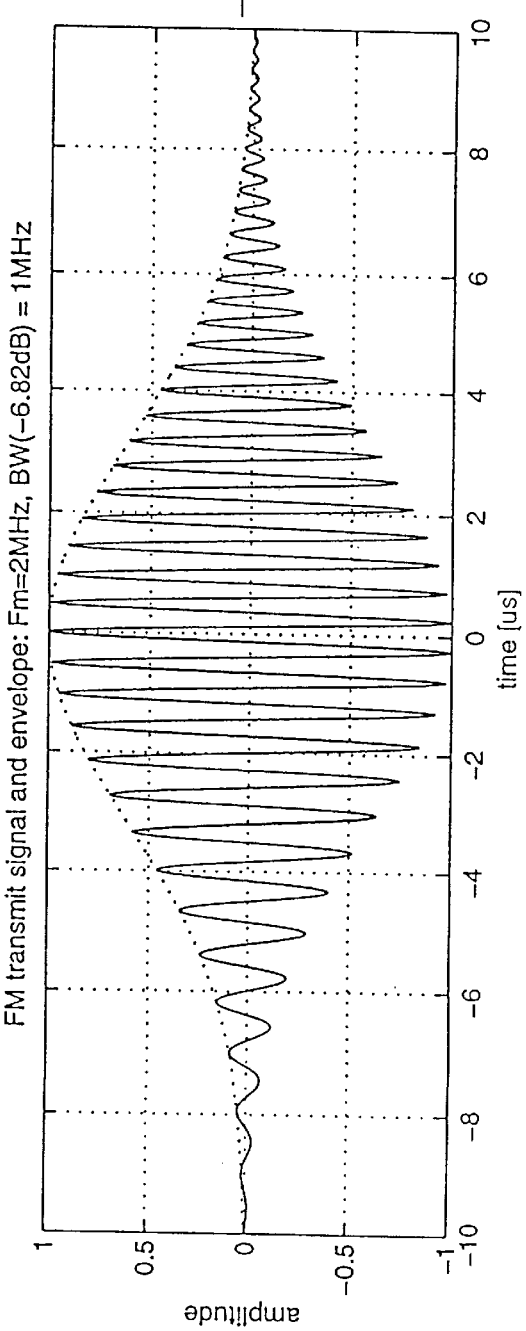
Figure 6C:
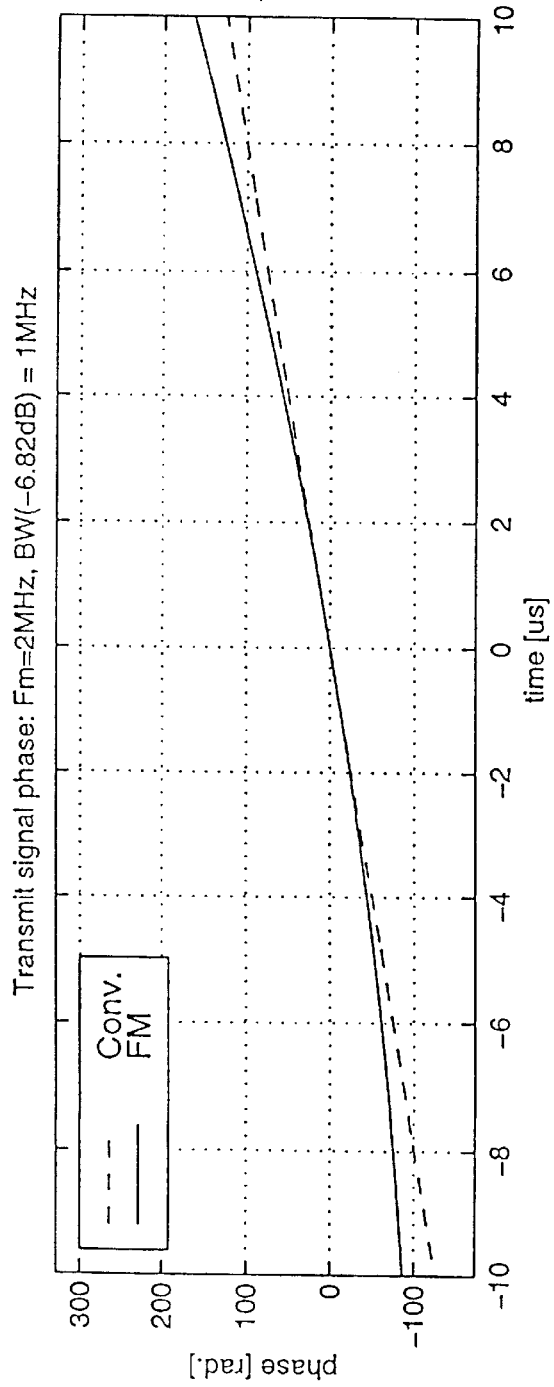
Figure 6D:
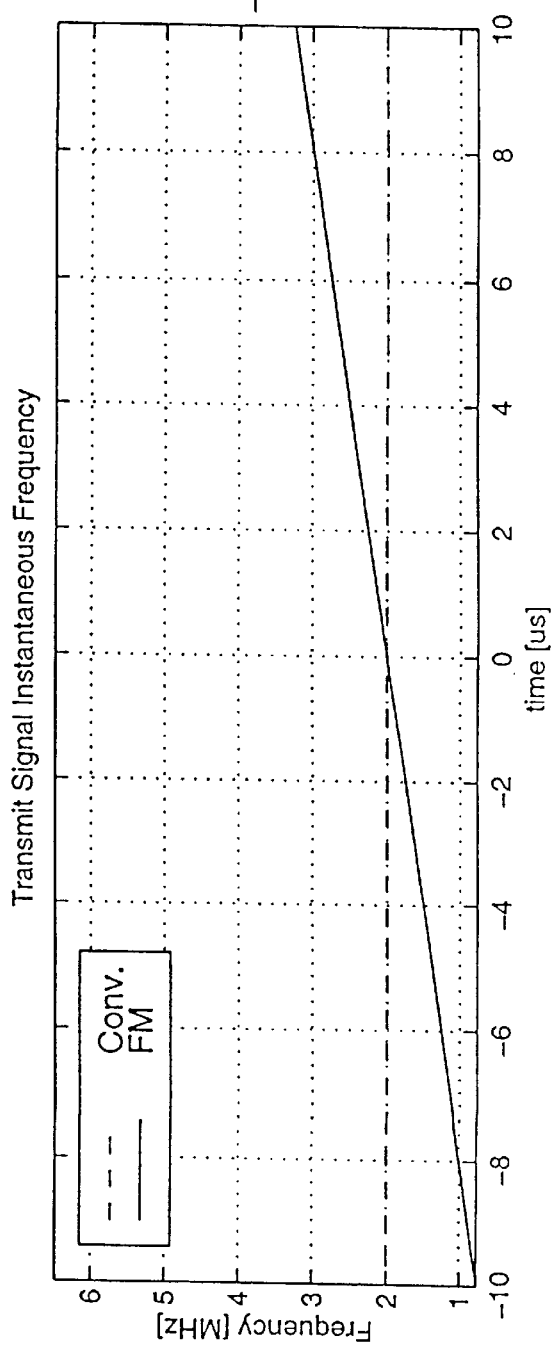
Figure 9:
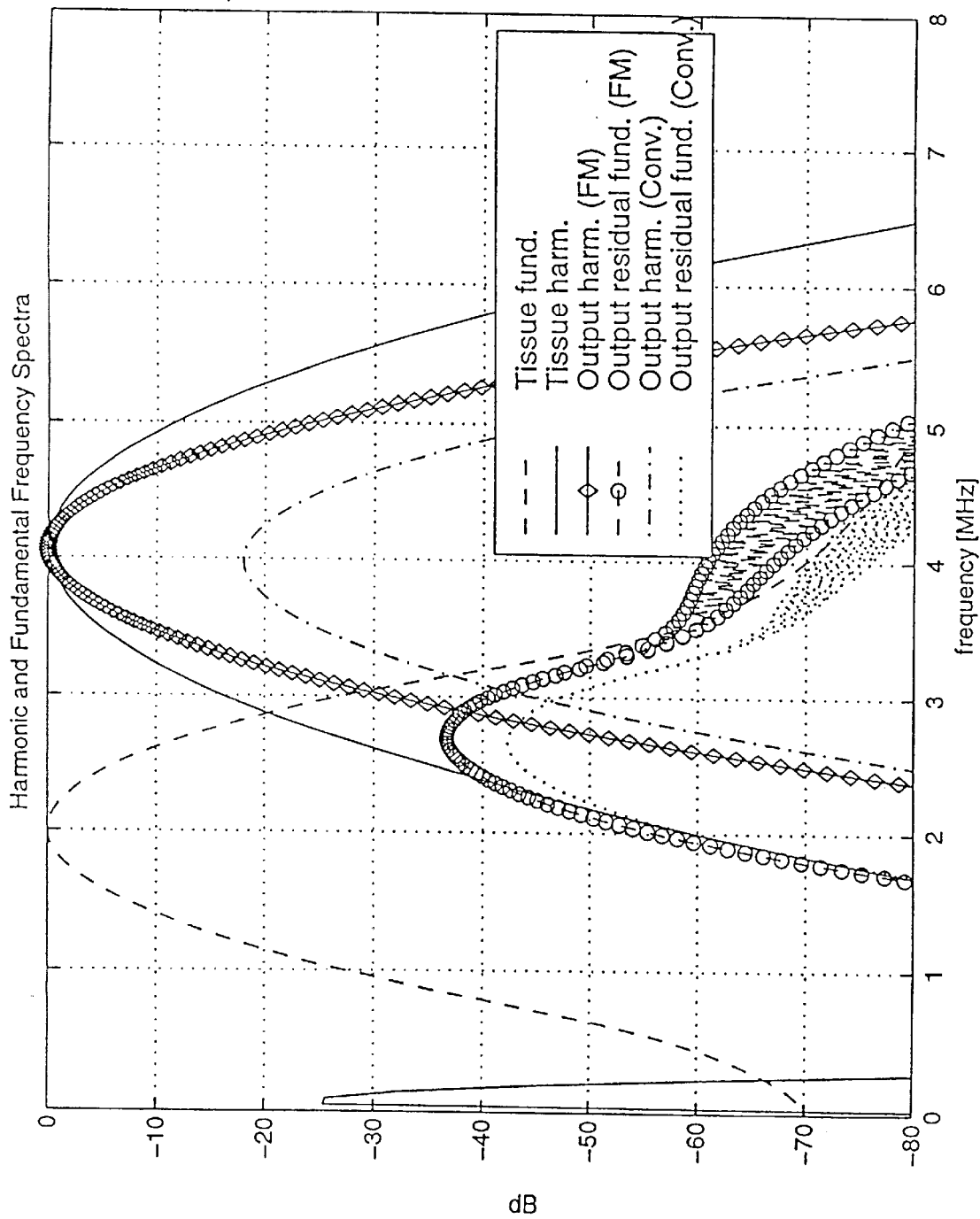
FIG. 9 corresponds to FIG. 5, except that the coded pulse is that of FIG. 6b.

FIGS. 5 and 9 show the tissue and detected output signals in the frequency domain for the conventional and coded transmit signals. These figures illustrate that the −6.82 dB bandwidths of the tissue fundamental and the tissue second harmonic signals remain constant, independent of the specified temporal duration of the transmitted signals. Also, the difference in detected signal energy for the returns from the coded transmit signals as compared to the returns from the conventional transmit signals is shown for the two cases. Although the output signal for the larger of the two time-bandwidth products would be greater for identical peak transmit signal levels between the two coded cases presented, all spectra in FIGS. 5 and 9 have been normalized for each case independently by the harmonic tissue signal peak for the coded pulse-compression technique. Thus the maximum spectral amplitude for the signal outputs is always zero decibels. This normalization emphasizes the differences in the tissue harmonic signal levels for conventional transmit signals and the residual fundamental signal levels after harmonic receive filtering.

Many modifications to the preferred embodiment and to the foregoing example are possible, including the following:

1) General modulation of amplitude, a(t), and phase, φ(t).

Figure 22:
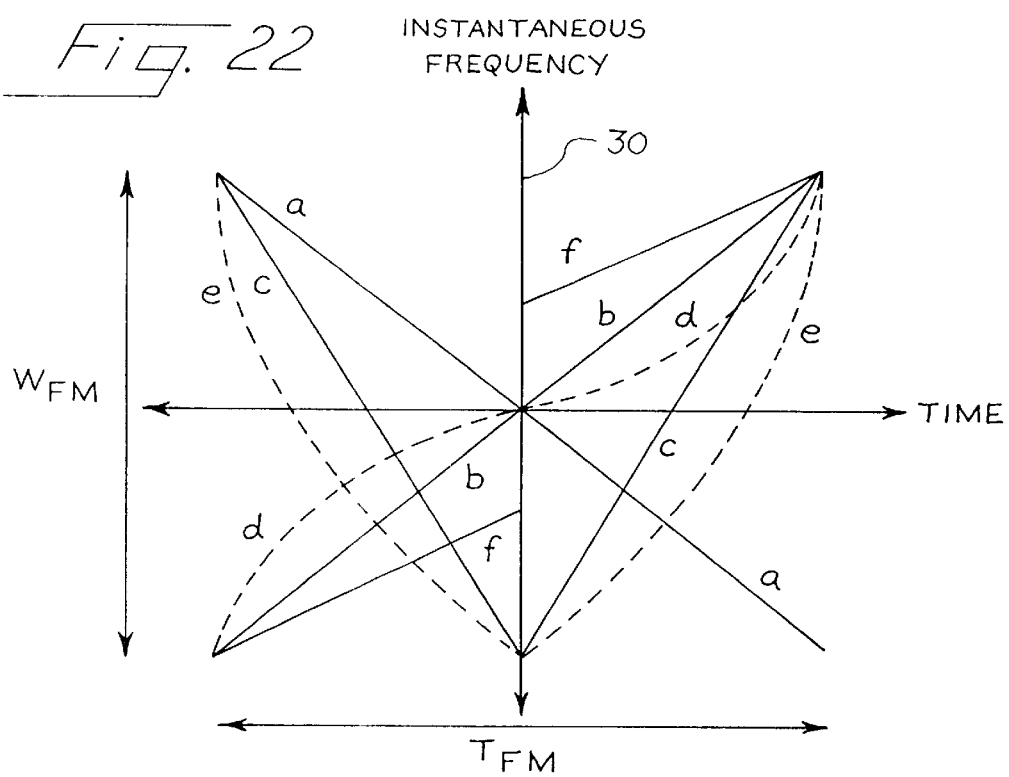
FIG. 22 is a diagram of alternative frequency modulation functions versus time that can be used to form coded transmit signals and/or pulse- compression receive filters in alternative embodiments.

An example of a Gaussian amplitude modulated envelope with nonlinear quadratic phase (or linear frequency) modulation versus time was given above, but many different types of amplitude and phase modulation functions can be used in the transmitter and in the pulse-compression receive filter. FIG. 22 shows a few examples of linear, nonlinear, discrete, and continuous instantaneous FM functions versus time. These functions are the temporal derivative of the phase modulation (PM) functions. The functions are preferably defined within the scope of the pulse temporal duration $T_{FM}$ and the desired frequency span WFM. Note, the line 30 is situated at one-half the envelope duration. These are examples and are not exhaustive. Examples of linear FM (quadratic PM) functions are shown labeled a, b, and c. Two piecewise linear FM functions are functions f and c. Two nonlinear FM functions are labeled d and e. Note that the modulation functions c and e are symmetric about the line 30 while the other functions are asymmetric about line 30.

Figure 23:
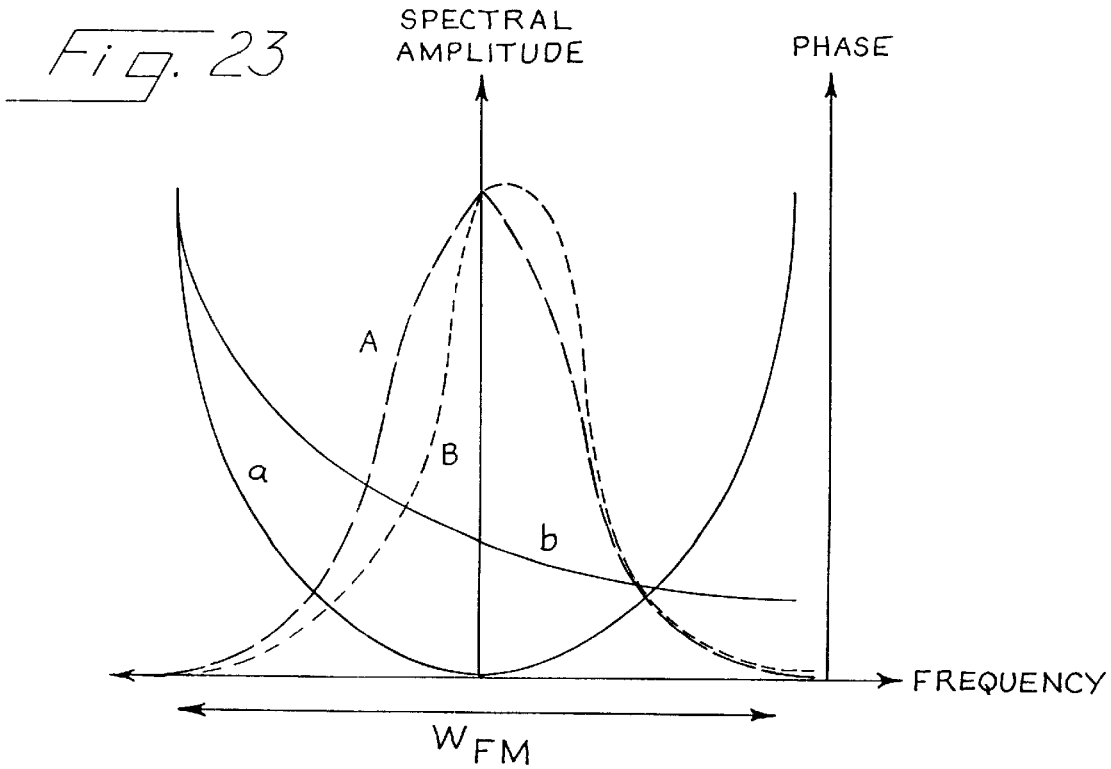
FIG. 23 is a diagram of alternative phase functions versus frequency and signal spectra that can be used in alternative embodiments.

FIG. 23 shows a few examples of symmetric and asymmetric nonlinear phase functions versus frequency together with general signal amplitude spectra. Spectra A and B, shown as dashed lines, are representative of signal spectra at the transmitter or input of the pulse-compression filter. Phase functions, a and b, shown as solid curves are examples of symmetric and asymmetric functions. Function a is symmetric about amplitude spectrum A or asymmetric about amplitude B. Function b is asymmetric about amplitude spectrum A and B.

Figure 24:
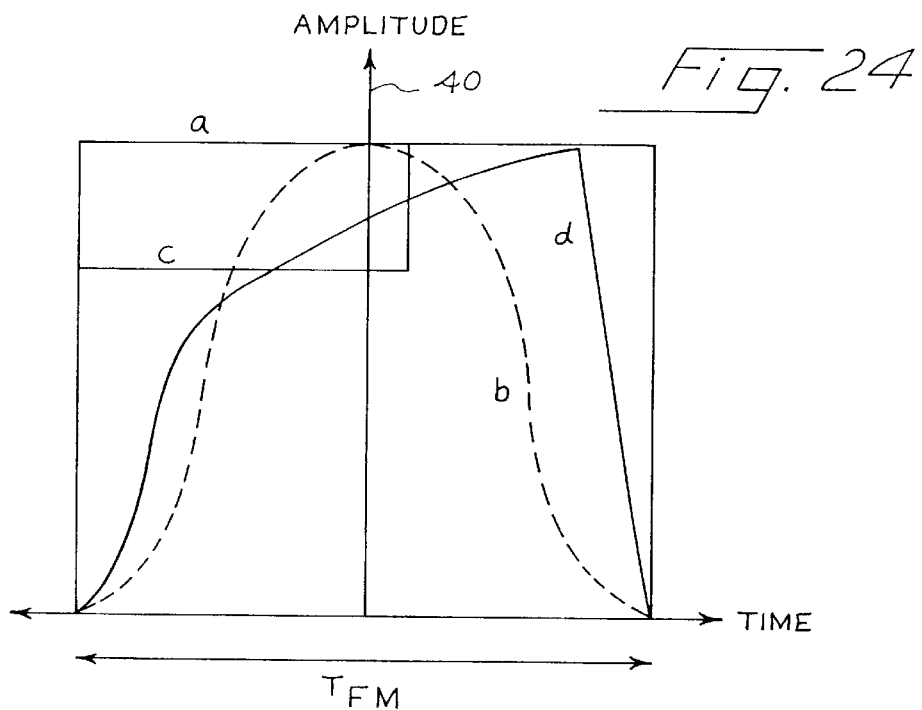
FIG. 24 is a diagram of alternative amplitude modulation functions versus time that can be used in alternative embodiments.

FIG. 24 shows a few examples of symmetric and asymmetric amplitude modulation functions versus time with respect to the line 40 located at one-half the envelope duration. Functions a and b are symmetric amplitude profiles while functions c and d are asymmetric profiles. These types of functions can be applied independently in the transmitter and pulse-compression receiver depending on the desired system over-all spectral response. Asymmetric functions are particularly useful to maximize SNR by compensating for spectral shaping created by tissue attenuation, acoustic diffraction, and impulse responses from system and transducer designs.

Some of these combinations illustrated in FIGS. 22, 23, and 24 may be preferred for specific system designs. Examples are given below.

1a) Phase modulation functions other than those that vary linearly or quadratically versus time such as nonlinear instantaneous frequency modulation functions may be preferred when constant amplitude pulses, such as function a in FIG. 24, are transmitted. The use of quadratic phase modulation (or linear FM) with constant amplitude modulation may produce clinically unacceptable range lobes, but amplitude modulation functions other than constant amplitude may not be available in the transmitter. Constant or uniform amplitude modulation is popular among commercial ultrasound manufacturers due to the reduced cost of these types of transmitters as compared to more sophisticated transmitters with non-uniform amplitude modulation such as the Programmable Waveform Generator (PWG) sold by Acuson Corporation under the tradename Sequoia. With constant amplitude modulation, nonlinear FM may be used to preferentially shape the pulse-compression output spectra to help suppress high range lobes. The unwanted range lobes can alternatively or further be reduced by proper non-uniform symmetric or asymmetric amplitude modulation in the pulse-compression receiver. The potential disadvantage to non-uniform amplitude modulation in the receiver is lost SNR. Nonlinear FM can eliminate the need for additional receive amplitude modulation and thus maximize SNR with constant amplitude transmitted pulses.

1b) Another example where uniform amplitude modulation may actually be preferred and nonlinear FM used, irrespective of the types of amplitude modulation available in the transmitter, is for near field harmonic imaging. Imaging near the face of the transducer places a limit on the expanded pulse lengths since receive circuitry can not be turned on until the transmitters have been turned off, at least for systems that use the same transducers to transmit and receive ultrasonic energy. Also, the SNR may be poor if harmonic energy is generated solely from tissue nonlinear propagation. If maximum energy is to be transmitted into the tissue over the shortest window of time, a uniformly amplitude modulated waveform is preferred. To maintain acceptable range lobe levels nonlinear FM may be used.

1c) The phase modulation function may be randomized which, again, can be beneficial for those systems constrained to uniform amplitude modulation. By controlling the instantaneous frequency of the transmitted waveform, the time between the signal zero crossings can be precisely controlled to generate pseudo-random sequences. After receive filtering with the matched filter response, a temporally compact output is produced which yields excellent axial detail resolution and improved SNR. Further, if range lobes are unacceptable and nonuniform amplitude modulation is not available, a second complementary transmit firing, with the expected loss in frame rate, may be used to accentuate the main temporal lobe of the output signal while generating secondary range lobes with polarities opposite to those associated with the initial transmit firing. These two separate outputs can be added before display processing to help suppress the unwanted range lobes since the opposite polarity range lobes will cancel. An example of these types of complementary codes is the Golay codes described in M. J. E. Golay, *Complementary Series*, IRE Transactions on Information Theory, Volume IT-7, Number 4, October, 1961.

Two important aspects should be noted about the application of various forms of these types of codes to harmonic imaging, such as binary codes, which may include Golay codes or the well known Barker codes. First, in order to produce an inverted version of a second harmonic pulse, as is required for most of these codes, the fundamental transmit pulse must be shifted by plus or minus 90 degrees. For example, to realize second harmonic signals of the form $$\mathrm{Re}\{a^2(t)e^{j2\pi 2f_m t} - (a^2(t-T)e^{j2\pi 2f_m(t-T)})\}$$

and $$\mathrm{Re}\{a^2(t)e^{j2\pi 2f_m t} + (a^2(t-T)e^{j2\pi 2f_m(t-T)})\}$$

where T is the time between the two pulses for this two pulse example, the transmitted signals should have approximate form $$\mathrm{Re}\{a(t)e^{j2\pi f_m t} + j(a(t-T)e^{j2\pi f_m(t-T)})\}$$

and $$\mathrm{Re}\{a(t)e^{j2\pi f_m t} + (a(t-T)e^{j2\pi f_m(t-T)})\}.$$

Second, since the harmonic signal is generated by a nonlinear process, the two components of the transmitted signal should be sufficiently separated in time by time T to minimize overlap. Otherwise, a third undesired cross-product term would appear in the harmonic signals. By way of explanation, the harmonic waveforms shown above are examples of coding using complementary Golay codes. In addition, the first of the two waveforms is an example of a transmit waveform coded using the simplest Barker code of size two.

1d) Asymmetric phase functions versus frequency, i.e, functions like function b in FIG. 23, may be preferred for maximizing the SNR while maintaining accurate decoding in the pulse-compression receiver. Since frequency dependent attenuation preferentially attenuates higher frequency components more than lower frequency components, a receiver that tracks the returned spectral energy both in spectral width and center frequency can maximize SNR. One method to selectively position the depth-dependent spectral energy within a given baseband filter is to vary the demodulation frequency as a function of depth. If the SNR is to be maximized without unwanted image artifacts while varying the demodulation frequency, the receive filter can incorporate asymmetric phase functions and vary the filter impulse response with depth. This dynamically varying receive filter may be preferred.

If a depth-dependent receive filter is not available, other methods may be used to minimize inaccurate decoding or image artifacts with a fixed receiver.

One method is to fix the demodulation frequency to be constant with depth and keep the phase functions symmetric about a specific frequency, such as the transmit modulation frequency.

Another alternative, in particular for quadratic phase modulation, is to temporally delay the receive signal as a function of depth before it is filtered with the pulse-compression function. Increasing delays are added with increasing depths to maintain accurate decoding.

Yet another alternative is to maintain a symmetric, depth-independent, phase function with a depth dependent demodulation frequency and accept the possible artifacts. For some phase functions or corresponding FM functions the image artifacts may be tolerable.

1e) A transmitted pulse with temporally discrete segments with each segment consisting of independent amplitude and nonlinear phase modulation functions may be preferred. An example with this type of characteristic was given in FIG. 22 labeled function f. Function f incorporates two independent nonlinear quadratic PM functions (or piecewise linear FM functions as shown). This type of code that effectively consists of subcodes can be used to extract information from the tissue at two closely spaced time intervals or used to preferentially excite contrast agent harmonics. One temporal segment with a unique amplitude and phase function may preferentially excite or nucleate a mode of vibration that depends on the existence of the other coded segment. This type of code can be used to optimally detect fractional harmonic energy such as subharmonics. Of course multiple codes can be designed to overlap in time, which is effectively the addition of two codes. In this example with two different segments, the pulse-compression receiver can decode the energy associated with one or both segments. If one segment was used to excite a specific vibration mode, another segment can be used for imaging presentation. A specific example where these types of codes can be useful is where a low amplitude transmitted subharmonic is used to nucleate the growth of subharmonic energy from higher amplitude fundamental energy, also included in the transmitted pulse. This example is described in detail in co-pending U.S. patent application Ser. No. 09/287,603, filed on the same date as the present specification and now U.S. Pat. No. 6,117,082 and hereby incorporated by reference.

2. Any type of transducer, including multi-dimensional transducers—the invention is not limited to piezoelectric transducers or those commonly available on commercial ultrasound systems. For example, the invention may be practiced with electrostatic transducers.

3. Different time-bandwidth products and/or types of amplitude and phase modulation per transmit firing—for example, the time-bandwidth product may be depth dependent when two or more transmit foci are used. To maintain good near field imaging a smaller time-bandwidth product may be preferred for the shallowest focus.

4. The encoding transmitter and decoding receiver can be implemented in different forms. The transmitter and receiver can utilize digital and/or analog circuitry, and the transmit waveform does not necessarily demand a mixer. An example of a suitable transmitter is disclosed in U.S. Pat. No. 5,675,554, "Method and Apparatus for Transmit Beamformer". For example, a simple, digitally-stored waveform can be amplified without a mixer, or an analog oscillator can be swept in time through different frequencies while varying the amplitude. An impulse generator may be used with appropriate complex filters to implement the filters and to generate the desired transmit codes. The receive filtering is not limited to the architectural example given. For example, the demodulation stage need not occur after complete beamformation; instead it can occur on each or a subgroup of receive channels before complete beamformation. Further, receive filtering need not occur at baseband. The complex filtering can be implemented at an intermediate frequency.

5. The invention is not limited to fundamental or second harmonic signals. Any order integer harmonic or fractional harmonic may be decoded.

6. The invention can be used with simultaneous or temporally sequential acquisition and processing of a coded pulse-compression image of the current invention with another type of image, color or B-mode. Examples include the following:

a) Fundamental or any order harmonic B-mode image with a coded pulse-compression fundamental or any order harmonic B-mode image.

b) Fundamental or any order harmonic B-mode image with a coded pulse-compression fundamental or any order harmonic image of motion.

c) Fundamental or any order harmonic image of motion with a coded pulse-compression fundamental or any order harmonic B-mode image.

d) Fundamental or any order harmonic image of motion with a coded pulse-compression fundamental or any order harmonic image of motion.

7. The invention can be used with any pre-detected combination of two or more separate beams, spatially collinear or spatially distinct. The individual beams in the combination may have delay profiles with identical amplitudes, frequencies, and phases or may have different amplitudes, frequencies, or phases. An example of this embodiment would include the addition of two beams after pulse-compression receive filtering with opposite polarity transmit phasing to provide improved fundamental signal rejection/cancellation and therefore improved signal bandwidth and axial detail resolution. The associated transmit beams may be spatially aligned as in conventional pulse inversion imaging (e.g. Chapman U.S. Pat. No. 5,632,277) or spatially distinct as described in co-pending U.S. patent application Ser. No. 09/282,306, which is hereby incorporated by reference in its entirety.

Specific Embodiments

The system of FIG. 1 can be used to implement any of the following imaging methods.

1. Multi-mode displays:

Coded nonlinear phase modulated pulse-compression or non-coded images (fundamental or harmonic) may be displayed in combination with a coded pulse-compression color motion image (fundamental or harmonic). Similarly, coded spectral Doppler detected parameters-vs.-time waveform(s) (fundamental or harmonic) may be displayed in combination with any type of B-mode or color image, coded or non-coded.

2. The firing of two or more simultaneously transmitted beams:

For B-mode or 2D color motion imaging, two or more ultrasound beams may be transmitted simultaneously to increase frame rates. For spectral Doppler processing, where velocity-energy spectra are commonly displayed versus time for a selected gate, two or more ultrasound beams may be transmitted simultaneously to allow the display of multiple spectra-vs.-time waveforms for multiple independent gates. Each transmit delay profile, corresponding to a selected focus, can be encoded with a unique code, and a matched decoding receive filter for each unique code can be used to maintain adequate acoustic isolation between the at least two ultrasound foci.

Figure 10:
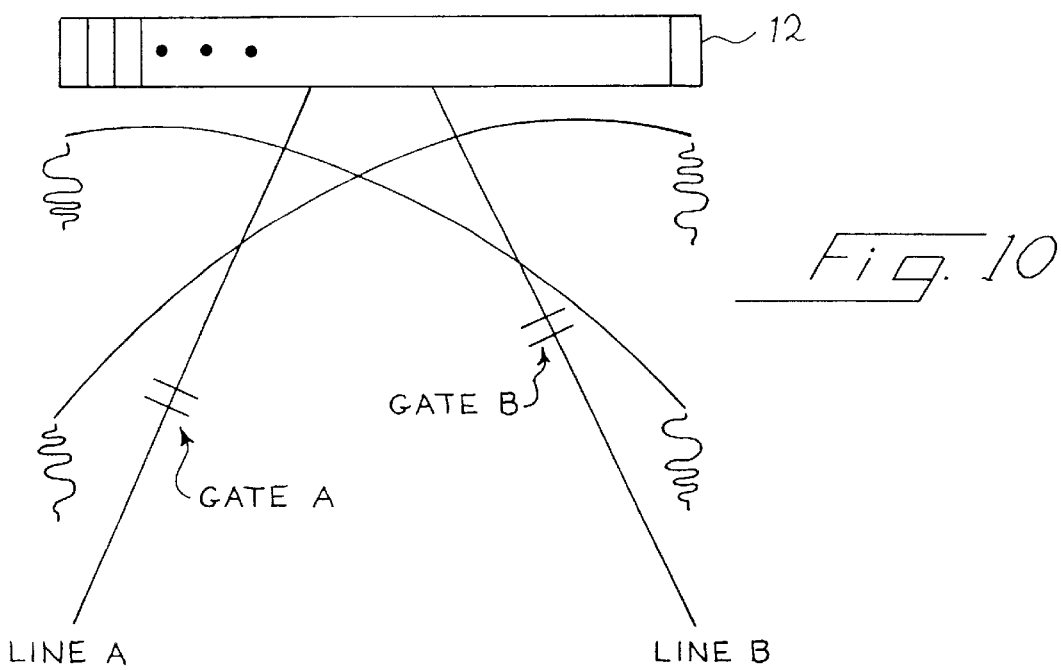
FIG. 10 is a schematic diagram of an imaging mode in which two separately coded transmit beams are launched from the same aperture along two spatially distinct scan lines.
Figure 11:
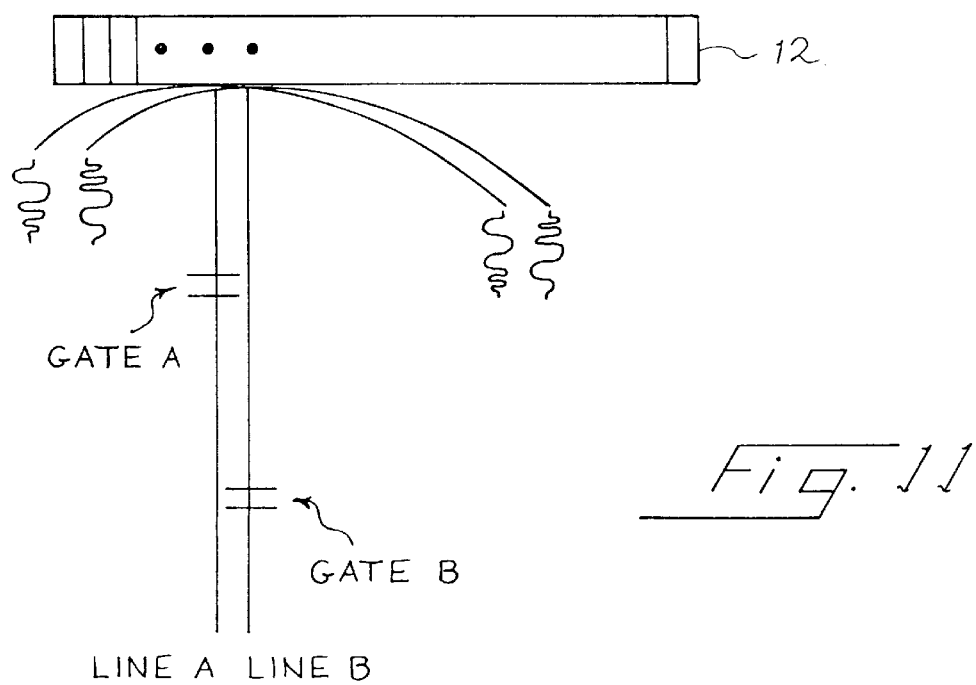
FIG. 11 is a schematic diagram of an imaging mode in which two separately coded transmit beams are launched from respective overlapping subapertures of the transducer array.

Two examples of this type of processing with two unique delay profiles, corresponding to transmit beams A and B, are shown in FIGS. 10 and 11. In FIG. 10, all of the elements in the array contribute to transmit beam A as well as transmit beam B, and both transmit beams A, B therefore use the same aperture, the full aperture of the transducer array 12. In FIG. 11, the transmit beams A, B are formed from respective overlapping subapertures of the full aperture of the array 12. The transmit waveforms for each delay profile can be uniquely encoded and one or more receive filters can decode the returned signals such that interference between the beams is reduced to an acceptable level. For each unique transmit delay profile an associated unique receive filter impulse response decodes the returned signals such that returned signals from other transmit delay profiles appear as noise and do not substantially contribute to the focus of interest. Unique encoded delay profiles for multiple transmit foci located on different ultrasound lines may be generated for each transmission from a single group of transducer elements. Also, one or more receive beams may be associated with each transmit focus and therefore, ultrasound line. Being able to generate more than a single line from a single transmission from a group of elements allows increased frame rates for a specified final image line density. This approach can be extended into three dimensions using one dimensional or multidimensional transducers.

By transmitting two or more beams simultaneously, fewer transmit firings are necessary in B-mode or 2D color motion imaging to generate an image frame, thereby increasing frame rates in fundamental and harmonic imaging, both with and without contrast agents. Multiple receive beams may also be acquired from each transmit beam. When spectral Doppler processing is used with the pulse-compression techniques described herein, multiple independent gates may be placed by the user. Multiple parameters-spectra versus time waveforms may be shown simultaneously without significant loss in waveform quality. For example, in FIGS. 10 or 11, gates A and B, can be placed independently.

Figure 12:
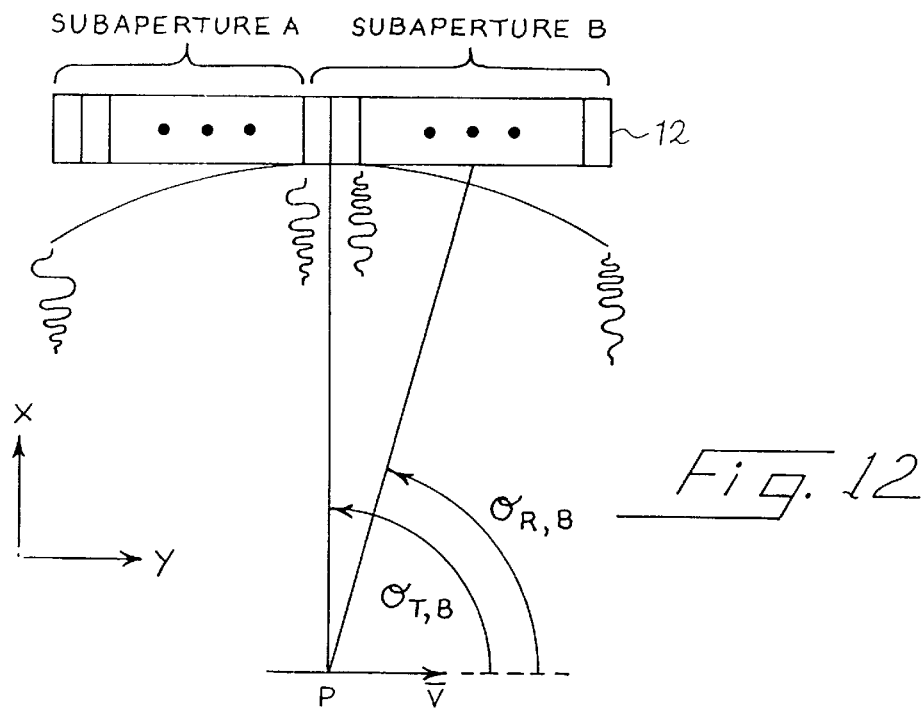
FIG. 12 is a schematic view of an imaging mode in which two transmit beams are launched from respective nonoverlapping subapertures during a single transmit event.

3. Subaperture encoding:

Subapertures within an active aperture may be uniquely encoded and decoded to improve sensitivity to non-axial motion for multidimensional motion imaging and spectral Doppler imaging. Split aperture encoding (i.e. separate codes for non-overlapping subapertures) or subaperture encoding (i.e. separate codes for respective subapertures that may or may not overlap) for a single transmit-receive delay profile pair may be used to improve directional sensitivity and frame rates. An example of this type of processing is shown in FIG. 12 for a simple, split, two-subaperture configuration associated with one transmit delay profile. A delay profile for the full aperture of the transducer 12 is encoded with two different transmit waveforms. One subaperture on the left, subaperture A, uses one code while the other subaperture on the right, subaperture B, uses a different code. Upon reception, two receivers decode the signals, one pulse-compression receiving filter impulse response per subaperture. As an example, a linear frequency modulation function that begins at a low frequency and increases the modulation frequency with time can be used on one subaperture, while the converse can be used on the other subaperture.

There are three primary advantages to this technique. The first advantage is increased frame rates, since two separate transmit firings are not needed to acquire receive signals for the two subapertures. The second advantage is increased sensitivity to components of motion that are parallel to the face of the transducer. This improves the accuracy of detecting multidimensional motion. Considering the example illustrated in FIG. 12 for subaperture B, maximum sensitivity to motion in the y direction is obtained with minimal values for the angles $\theta_{T,B}$ and $\theta_{R,B}$, where the first subscript denotes transmit (T) or receive (R) and the second subscript denotes the subaperture. Since many sensitive motion detection techniques, like color Doppler motion imaging, rely upon detecting pulse-to-pulse differences in the main carrier frequency, encoding a subgroup of elements away from the center of the array increases the lateral (y-direction) spatial frequency content at point P. For a given velocity V, increasing differences are detected when the center of the transmit-receive subaperture pair for subaperture B is moved toward the end of the physical array. For example, in color Doppler motion imaging, a larger Doppler shift is detected for smaller angles $\theta_{T,B}$ and $\theta_{T,B}$. In the example given in FIG. 12, subaperture-specific encoding moves the angle of greatest signal sensitivity on transmit to the center of subaperture B, thereby making it similar to the angle of greatest sensitivity on receive. Unique encoding of each subaperture provides increased sensitivity to multidimensional motion and allows the direction of multidimensional motion to be estimated. A third advantage with simultaneous coding and simultaneous reception is the suppression of motion artifacts as compared to a conventional technique of two firings, one for each subaperture. If multi-dimensional directional information is desired at a specified point in space for a given time instant, estimates of this information using two firings may be corrupted by nonuniform motion between the firings.

Examples of two imaging techniques where directional information can be useful are color Doppler motion imaging of blood flow and tissue movement, and strain imaging. An example where this technique can be used to further improve a preexisting technique for multidimensional motion estimation is the application of subaperture encoding to the system disclosed in U.S. Pat. No. 5,522,393. In this patent two or more receive subapertures share a single transmit aperture, but further directional sensitivity may be obtained by breaking the transmit aperture into coded subapertures.

In addition to the advantages for multidimensional motion detection, such as the display of true vector estimates at many points in space, the spectral Doppler cursor may be automatically placed with improved accuracy. The spectral Doppler cursor is typically manually placed by the user in an effort to estimate the direction of motion. The system subsequently uses the selected direction estimate to adjust the velocity estimates based on the cosine of the angle between the insonification direction and the direction of motion. The system disclosed in Banjanin et. al. U.S. Pat. No. 5,454,372 uses the concept of subapertures to detect directional information on receive for the automatic placement of the cursor, but makes no mention of encoded waveforms. Encoded waveforms can improve the estimate of direction and therefore improve the estimation of motion in spectral Doppler.

4. Interpulse encoding in spectral Doppler processing:

Pulse-specific encoding in conventional spectral Doppler for a single pre-selected gate may be used to provide more accurate spectral parameter detection. To avoid strong returns from areas other than a selected gate, the pulse repetition interval (PRI) is typically set based upon the location of the gate from the transducer. This interval fixes the maximum detectable velocity, $V_{max}$ (assuming the direction of motion is parallel with the ultrasound line), according to the well known relationship $$V_{max} = \frac{c}{[4(PRI)f_o]},$$

where c is the speed of sound and $f_o$ is the main carrier frequency. If pulses are fired at a rate greater than 1/PRI, larger unaliased velocities may be detected or extra samples may be acquired; however, motion from areas other than the gate of interest can introduce inaccuracies in the displayed parameters-vs.-time waveform. These inaccuracies may exist if returns from other locations arrive at the transducer at the same time as the returns from the gate of interest.

During the fixed time over which the data associated with a parameters-spectrum, such as a velocity-energy spectrum, is acquired, additional uniquely coded pulses may be used to increase the sampling rate of the motion of interest. The additional information provided by the additional pulses may be utilized in two ways. First, the additional pulses, since they are transmitted at a higher rate, can be used to measure larger unaliased velocities and the energy associated with these higher velocities. Second, the final set of pulses can be decimated into multiple sets of data, each with an effective sampling rate less than the actual coded sampling rate, and the multiple calculated parameters-spectra can be averaged to reduce estimation inaccuracies.

This latter method does not alter the maximum detectable velocity range as does the former method, but instead provides additional sets of data. These methods can be applied in fundamental and harmonic imaging, both with and without contrast agents.

Figure 13:
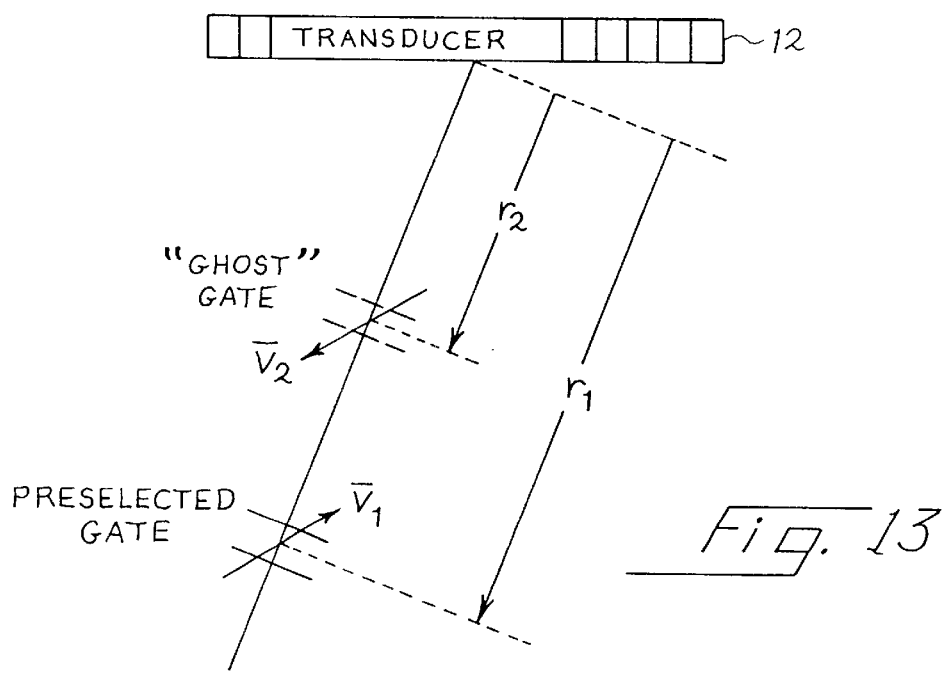
FIG. 13 is a schematic diagram of a spectral Doppler imaging method.
Figure 14:
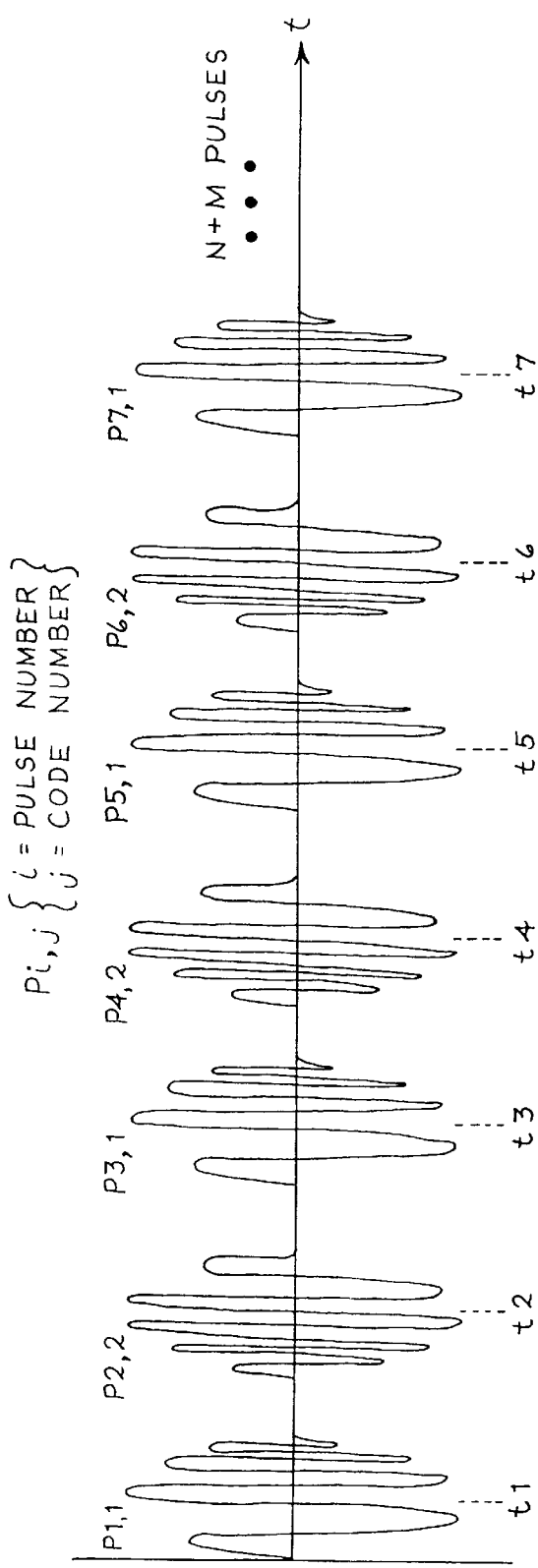
FIG. 14 is a waveform diagram of a series of coded transmit pulses, in which two separate transmit pulse codes alternate in time.

The interpulse encoding disclosed here can be used as follows. For a preselected gate location and size, N primary pulses are transmitted at a rate as determined by the two-way propagation time between the gate and the transducer. As illustrated in FIG. 13 for a preselected gate and a "ghost" gate, the primary pulse repetition rate (PPRR) for the preselected gate is $c/(2r_1)$. To increase the number of samples and the actual pulse repetition rate, M secondary pulses are transmitted in between the primary pulses. The secondary pulses are transmitted with a coded waveform that is different from the primary pulses. Each additional secondary pulse that is transmitted between two primary pulses is encoded with a unique code. An example using one secondary pulse in between two primary pulses is shown in FIG. 14. For this example two unique codes are used and the transmission of each code alternates. More than two codes are preferably used when two or more secondary pulses are transmitted between two primary pulses.

Upon reception, demodulation, and quadrature signal separation (all well known in the art), each unique coded waveform is decoded with a preferred matched pulse-compression filter. An example for the case described here might utilize two receive filters that are alternately enabled and disabled in time. Alternatively, two parallel receive filters can simultaneously filter the signals. After receive filtering, the signals are preferably integrated over the range gate size and sampled. A single sample is generated for each transmitted pulse, for a total of N+M samples. This sample set and possibly separate groups of subsets are processed using an FFT algorithm. Parameters such as the velocity spectrum, energy spectrum, variance, mean velocity, maximum velocity, mode velocity, maximum energy, and combinations thereof may be displayed versus time. These post-decoding signal processing steps are well known to those skilled in the art of spectral Doppler processing. The steps described here are simplified examples and are not further disclosed since spectral Doppler processing is common in the industry.

Unique interpulse coding improves the accuracy of detecting spectral parameters at a preselected gate when significant energy from other coded waveforms arrives at the same time, since energy from other codes does not experience the same coherent gain when passing through the receive filter. Referring to FIGS. 13 and 14, in one example, pulses $P_{1,1}$ and $P_{2,2}$ are transmitted at times to and $t_2$, respectively, and will arrive at the same time $t_3$, associated with the round trip propagation time from the preselected gate. Any motion within a "ghost" gate, such as $v_2$, at a distance $r_2$, where $r_2$ is equal to one half rl, can introduce unwanted Doppler shifts into the detected spectra associated with the desired gate at distance $r_1$. This occurs since the pulse $P_{2,2}$ is transmitted when pulse $P_{1,1}$ arrives at the preselected gate. By using separate, respective codes at times $t_1$ and $t_2$, and a receive pulse-compression decoder matched to the waveform at time $t_1$, signals from the "ghost" gate will be reduced at time $t_3$ and will experience less coherent gain per instant in time. This minimizes artifacts.

With respect to the two uses of the spectral Doppler interpulse encoding mentioned earlier, the time between primary pulses and secondary pulses alters the clinical utility.

If the time between any two pulses is constant, the acquired samples may be used to increase the maximum detectable velocities or to improve estimation accuracy without increasing the maximum detectable velocities. This is a matter of choice. If the secondary coded pulses are not used to increase the maximum detectable velocities, the final data set of N+M pulses may be decimated and each new data subset can be processed with an FFT algorithm. For example, every even-numbered pulse may be included in set one while every odd-numbered pulse may be included in set two. More than one secondary pulse between two primary pulses allows for three or more sets or subsets. A parameters-spectrum is preferably generated for each set and the spectra are averaged before display. If the secondary pulses are used to increase the maximum detectable velocities, the entire N+M pulses are processed with the FFT algorithm.

The methods disclosed here allow the estimation of multiple parameters, such as velocity or energy, for example, and utilize the well known and robust FFT algorithm for spectral Doppler processing.

If the time between any two pulses is not constant, the total of N+M pulses are preferably not used to increase the maximum detectable velocities since the total number of samples used to estimate a parameters-spectrum with the increased velocity limit would be equal to one plus the total number of secondary pulses that are fired between any two adjacent primary pulses. (This assumes that the time between the first primary pulse and the first secondary pulse is equal to the time between two secondary pulses adjacent in time.) This likely small number of pulses is often insufficient to produce clinically useful spectral Doppler waveforms with sufficient SNR and spectral resolution. Instead, the pulses are preferably processed to increase spectral estimation accuracy. Two or more subsets are generated from the N+M pulses and individual spectra are averaged together.

5. Interpulse encoding in multi-dimensional motion processing:

The encoding and decoding of each pulse used for estimating motion based upon the popular autocorrelation algorithm is identical to that described above in section 4. The difference between this method and the method for improving spectral Doppler processing is specific to the unique processing completed after the decoding process. Instead of processing the receive pulses with an FFT algorithm, an autocorrelation algorithm is applied at each sampled location within the selected image area. The algorithm estimates the mean velocity, energy and variance of the motion at each location.

Figure 15:
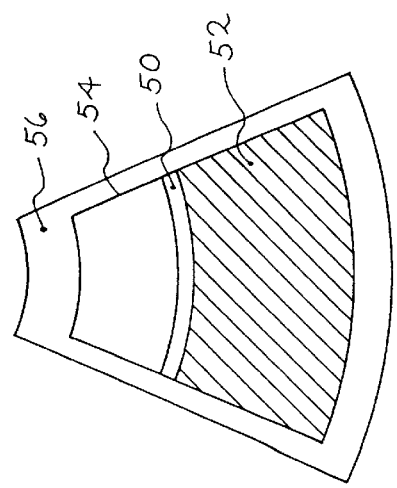
FIG. 15 is a schematic view of a color flow Doppler image.

A preferred display area for this embodiment is based upon an area being automatically selected for motion estimates. The preferred display method is illustrated in FIG. 15. In addition to the primary pulses whose PRI is determined by the initially selected maximum depth of the display area, any additional secondary pulses may impose a dead zone 50 within the selected area. Since the receivers will be corrupted by active transmitters of more significant signal strength, a dead zone will exist where motion estimates can not be accurately displayed. The extent of this dead zone in range will be determined by the difference between the beginning of the first transmitted secondary pulse and the end of the last transmitted secondary pulse for a given delay profile. More than one dead zone may exist if more than one secondary pulse delay profile exists between the delay profiles corresponding to two primary pulse transmissions. A preferred display area 52 of motion estimates is automatically selected based upon the dead zone that is closest in range to the maximum display area for motion estimates. An alternative display area 54 of motion estimates is provided at depths less than the dead zone 50. Alternatively, the initially selected display area may be used in its entirety with the image from the background area 56 showing through the dead zone(s) where motion estimates do not exist.

6. Coded pulses with pulse inversion harmonic Doppler imaging.

Figure 25:
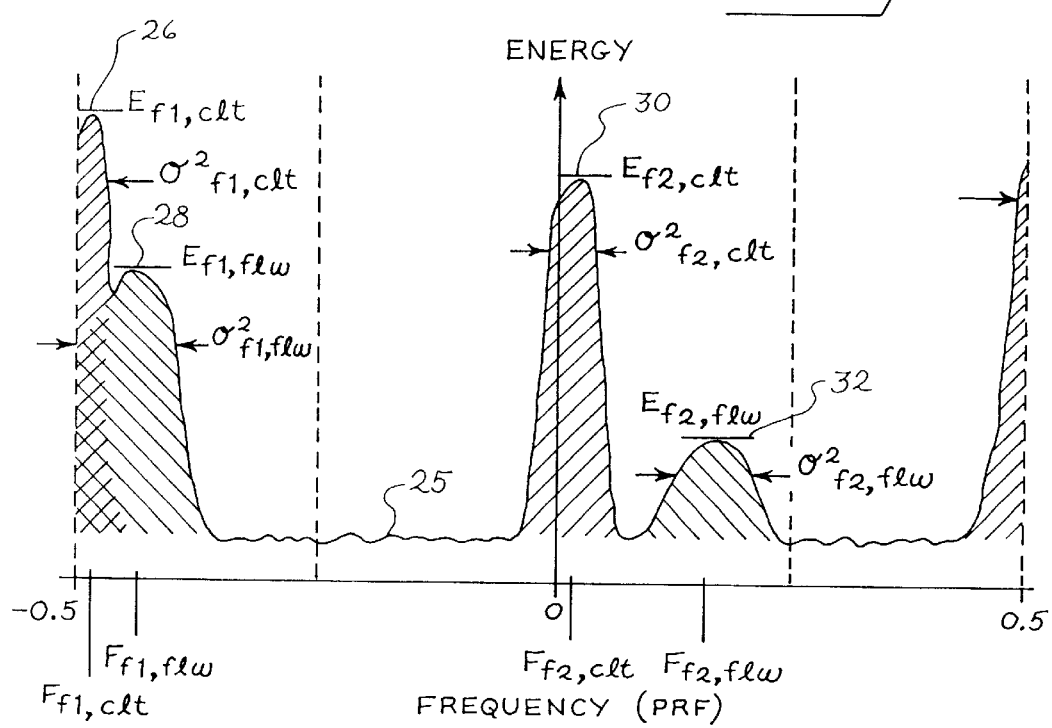
FIG. 25 is a Doppler frequency spectrum of an ultrasonic receive signal ensemble.

Coded pulses may be used to improve the SNR of pulse inversion harmonic Doppler imaging and improve the specificity of contrast agent detection. When there is insignificant agent disruption during a multiple pulse insonification, alternating polarity pulses can be used to spectrally separate fundamental and second harmonic Doppler signals. The nonlinear phase modulation function as presented in Equation 4 can be modified by adding a constant phase term that depends on the pulse index. For an ensemble of FSC transmitted pulses, with indices 1 to FSC, the new phase modulation function would be equal to $$\phi'(t)=\phi(t)+(n-1)$$

for each pulse of index n. By using alternating phase inversion, the fundamental and second harmonic Doppler spectra are separated as shown in FIG. 25. The Doppler frequency axis has been normalized by the pulse repetition frequency PRF (=1/PRI).

The spectrum 25 includes energy 26 responsive to clutter at the odd harmonics including the fundamental frequency, energy 28 responsive to flow at the odd harmonics including the fundamental frequency, energy 30 responsive to clutter at even harmonic frequencies, and energy 32 responsive to flow at even harmonic frequencies. Each of these responses is defined in terms of a peak energy, a frequency associated with the peak energy and a variance, where: $f_{f1,clt}$ and $f_{f2,clt}$ represent the mean frequency of clutter signals at the fundamental and even harmonic frequencies, respectively; $f_{f1,flw}$ and $f_{f2,flw}$ represent the mean frequency of flow signals at the fundamental and even harmonic frequencies, respectively; $\sigma^2_{f1,clt}$ and $\sigma^2_{f2,clt}$ represent the variance and proportional bandwidth of the clutter at the fundamental and even harmonic frequencies, respectively; $\sigma^2_{f1,flw}$ and $\sigma^2_{f2,flw}$ represent the variance and proportional bandwidth of the flow at the fundamental and even harmonic frequencies, respectively; $E_{f1,clt}$ and $E_{f2,clt}$ represent the energy of the clutter signals at the fundamental and even harmonic frequencies, respectively; and $E_{f1,flw}$ and $E_{f2,flw}$ represent the energy of the flow signals at the fundamental and even harmonic frequencies, respectively; $f_1$ indicates components due to the fundamental and possibly some odd harmonics; and $f_2$ indicates components due to even harmonics, such as the second harmonics.

By providing appropriate clutter or wall filtering, the clutter energy 26 and 30 of the fundamental and/or harmonic components, respectively, may be reduced. For example, a bandpass filter reducing energy associated with ½ and −½ the PRF and at the zero frequency reduces clutter of the fundamental and harmonic components. A lowpass filter may be used to remove clutter energy 26 of the fundamental component and in addition the fundamental flow energy 28 if desired. These types of filters maintain the flow signals of interest, such as the second harmonic flow signals, for subsequent parameter estimation in the processors 28 or 30 in FIG. 1. Because the fundamental signal components can be preferentially suppressed, while maintaining harmonic signals of interest, and nonlinear phase coding can be applied to each pulse for improved SNR, contrast agent specificity can be significantly increased beyond what is possible without the use of the disclosed pulse-compression techniques.

By way of example, the methods described above can be used in a medical diagnostic ultrasonic imaging system and method. A first coded ultrasonic pulse is transmitted into a body along a first transmit line. This transmit pulse is modulated with a first code as described above, and associated receive signals are acquired from the body in response to this first pulse. Then at least one second ultrasonic pulse is transmitted into the body. This second pulse differs from the first pulse in at least one of transmit envelope phase and polarity, and the second pulse is also coded. The first and second pulses can be directed along the same scan line as in conventional pulse inversion techniques. Alternately, the first and second pulses can be directed along spatially distinct but closely spaced scan lines, as described in co-pending U.S. patent application Ser. No. 09/282,396, filed Mar. 31, 1999, the entirety of which is hereby incorporated by reference. Receive signals are acquired from the body in response to the second transmit pulse. The acquired receive signals are then applied to a pulse compression filter, which may be of the type described above. The pulse-compressed receive signals associated with the first and second transmit pulses are then combined. As described in the above-referenced patent application Ser. No. 09/282, 396, this combination can be used to suppress fundamental components while enhancing second harmonic components, or to suppress second harmonic components while enhancing fundamental components. The combined compressed receive signals can then be processed in an image processing step in an imaging mode including color Doppler imaging, spectral Doppler imaging, motion processing imaging and strain imaging. If desired, a clutter filter can be interposed between the combining step and the image processing step, and in some embodiments, the clutter filter can be used to implement the combining step.

Alternative Embodiments

The above preferred embodiments describe the application of coded waveforms to tissue harmonic imaging and to imaging with contrast agents. Alternative embodiments are described here specific to contrast agent imaging. One alternative embodiment increases the temporal duration of the transmitted pulses at low pressure amplitudes to improve the SNR without destroying contrast agent. The temporally expanded excitation may be used to excite integer or fractional harmonics of the contrast agents. A second alternative embodiment increases the transmitted pulse durations with pressure amplitudes greater than the pressure amplitudes of the first alternative embodiment, but still less than a maximum, to improve the SNR while some contrast agent may be destroyed. Since optimal image contrast between detected nonlinear contrast agent signals and tissue signals may be obtained at transmit pressures less than the maximum, increased SNR can improve image quality and contrast.

Harmonic imaging of contrast agents increases SNR without loss of resolution when peak amplitudes are maintained and time-bandwidth product and pulse durations are increased as described above. However, there are additional advantages specific to contrast agent imaging such as imaging at low transmit voltages and hence low acoustic pressures. First, using low transmit voltages reduces destruction of the contrast agent. It is believed that a low acoustic pressure transmit pulse with long duration (high time-bandwidth product) will destroy less contrast agent than a compact, high acoustic pressure transmit pulse. Second, at reduced acoustic pressures, contrast agent nonlinear scattering may be increased relative to tissue scattering of the nonlinear propagated harmonic signal. One possible explanation for this is that, at higher acoustic pressures, there is a saturation effect in the scattering from contrast agents, as incident energy is either dissipated or converted to subharmonics or higher order harmonics rather than being converted to second harmonic scattering. The net result is that the contrast between contrast agent harmonic signals and tissue harmonic signals may be greater at low acoustic pressures than at higher acoustic pressures.

For these and possibly other reasons, it may be advantageous to image contrast agents at low acoustic pressures. However, at these lower acoustic pressures, SNR is significantly degraded. Pulse expansion and compression as described generally in this patent may be used to regain some of that SNR without sacrificing axial resolution. In fact, higher time-bandwidth products may be supportable for contrast agent imaging than for tissue harmonic imaging, as the reduction in peak amplitudes allows longer transmit pulses while staying below total pulse energy limits such as FDA limitations on time-averaged pulse power. Time-bandwidth products greater than 100 are impractical for a number of reasons. These long pulses cannot be accurately decoded without producing unacceptably high range lobes when conventional dynamic receive focussing is used, as is common in the industry. To avoid the inaccuracies associated with decoding long pulses with dynamic receive focussing, the pulse-compression filter can be replicated many times and each replica can be placed behind each receive beamforming channel before the dynamic time delays are applied. However, for most practical phased array transducer systems with many elements and system channels, the cost and complexity is prohibitive. Long pulses can also prohibit near field imaging, unless a stand-off pad is used, since conventional receivers cannot listen until the transmitters become inactive.

Nonlinear scattering from contrast agents is considerably more complex than nonlinear propagation through tissues, and models for this scattering may include a number of terms of order $x^2(t)$, where $x(t)$ is the incident transmitted pulse. For example, an accurate model may include terms in $$x^2(t),\ x(t)\frac{d^2}{dt^2}x(t),\ \left[\frac{d}{dt}x(t)\right]^2,\ \text{and}\ x(t)\frac{d}{dt}x(t).$$

However, for reasonably smooth phase variations in the transmit pulse and reasonable bandwidths, beneficial results may be obtained using the approximation that the second harmonic scattering from contrast agents is represented by $x^2(t)$. This leads to a scattefed second harmonic signal $$\text{Re}\{n(t)e^{j4\pi f_m t}\}$$

as in equation 8, where $$n(t)=a^2(t)e^{j2\phi(t)}$$

Of course, somewhat better results may be obtained by using a more accurate model for the nonlinear scattering and designing a receive pulse-compression filter to match the harmonic scattered pulse.

Further beneficial results are obtained by using nonlinear phase modulated transmit pulses with appropriately designed receive pulse-compression filters for imaging contrast agents in combination with alternately phased transmit pulses. Alternating transmit polarity techniques were described above, in particular, item 3 in the Description of FIGS. 2 Through 9 and item 7 of the examples of Preferred Embodiments. In general, reducing the transmit pulse voltage reduces second harmonic signal levels relative to fundamental signal levels from tissue nonlinear propagation, effectively reducing the suppression of the fundamental signals. In addition, using large time-bandwidth products on transmit and receive may result in a reduction in fundamental signal suppression due to finite filter lengths on transmit and receive. In either case, pre-detection combinations of spatially collinear or spatially distinct beams from alternating polarity transmit pulses may be used to increase suppression of the fundamental scattering from tissue. This improves contrast agent specificity and increases axial detail resolution without significant artifacts from unacceptably high fundamental signal levels. The nonlinear phase modulated transmit pulses disclosed above can be modified with an alternating phase term as such $$\phi'(t)=\phi(t)+(n-1)\pi$$

for each consecutively transmitted pulse of index n from 1 to the number of transmitted pulses.

Most of the prior discussion related to both tissue harmonic imaging and contrast agent imaging has concentrated on preferred embodiments in which the receiver performs a matched filtering of the received harmonic pulse. In some cases, it may be desirable to use either a narrower or broader bandwidth on receive than in the transmit pulse. In that case, the receiver is preferably chosen so that the phase distortion (phase vs. frequency) of the receiver compensates for the phase distortion (phase vs. frequency) of the received harmonic pulse. This may include a temporal frequency sweep on receive which differs somewhat from the frequency sweep of the harmonic pulse. For example, if the Gaussian transmit pulse described earlier is used, then the harmonic signal is approximated by $$e^{-2\pi\alpha t^2}e^{j2\pi\gamma t^2}e^{j4\pi f_m t},$$

with duration $T=(2\alpha)^{1/2}$, bandwidth $$W=\left[\frac{2(\alpha^2+\gamma^2)}{\alpha}\right]^{1/2},$$

and time-bandwidth product given by equation 19. If the receiver is to have a bandwidth $W_R$, then a Gaussian receiver is given by $$e^{-\pi(t/T_R)^2}e^{-j2\pi\gamma_R t^2},$$

where $$T_R=\frac{1}{W_R^2}+\left(\frac{W_R^2}{W^4}\right)[(TW)^2-1]$$

and $$\gamma_R=\frac{\gamma(TW)^2}{(TW)^2-1+\left(\frac{W_R^4}{W^4}\right)}$$

Other arbitrary bandwidth receivers may be designed, but in general, to optimally compress the expanded harmonic signal for best axial resolution, the receiver phase versus frequency is preferably determined to best undo the dispersion (phase vs. frequency) of the incoming harmonic signal. Another way to design pulse-compression receivers, especially when the receiver bandwidth is to be narrower than the harmonic signal bandwidth, is to design an appropriate matched receiver and filter the resulting output signal to reduce the bandwidth. This will ensure optimal compression and therefore axial resolution of the harmonic signal.

It should be noted that ideal transmit and receiver spectra may differ from Gaussian. This is particularly true for integer harmonic or subharmonic imaging, where the transmit and receive spectra are preferably designed to provide maximum axial resolution and signal energy while minimizing the contributions from either the fundamental or from undesired harmonics and subharmonics into the received signal.

One method for designing transmit pulses or pulse compression receive filters of arbitrary spectral shape makes use of the approximation that, for high time-bandwidth products and for monotonic instantaneous frequency modulation, $$|A(f_t)| = \left|A\left(f_m + \left(\frac{1}{2\pi}\right)\frac{d}{dt}[\phi(t)]\right)\right| \approx \frac{k_1|a(t)|}{\left(\left|\left[\frac{d^2}{dt^2}[\phi(t)]\right]\right|\right)^{1/2}},$$

where as described earlier,
A(f) is the pulse spectrum,
$f_t$ is the instantaneous frequency,
$f_m$ is the nominal modulating frequency,
φ(t) is the phase modulation function,
a(t) is the envelope magnitude,
and
$k_1$ is an arbitrary constant. For a quadratic phase modulated pulse with $$\phi(t) = \pi \gamma t^2$$

this reduces to $$|A(f_m + \gamma t)| \approx \frac{k_1|a(t)|}{(2\pi\gamma)^{1/2}}$$

or $$|A(f_t)| \approx \frac{k_1\left|a\left(\frac{f_t - f_m}{\gamma}\right)\right|}{(2\pi\gamma)^{1/2}}.$$

This approximation is most valid for high time-bandwidth products, but useful results may be obtained for time-bandwidth products as low as two or four, as may be useful for medical ultrasound applications. The harmonic spectrum associated with the above shaped pulse may be roughly approximated as $$\left|A\left(2f_m + \left(\frac{1}{2\pi}\right)2\frac{d}{dt}([\phi(t)])\right)\right| \approx \frac{k_2|a(t)|}{\left(\left|\left[\frac{d^2}{dt^2}[\phi(t)]\right]\right|\right)^{1/2}},$$

where $k_2$ is another arbitrary constant.

Alternative Hardware Implementations As suggested above, the widest variety of transmitter, receiver, transducer, decoder, image processor, and scan converter hardware can be adapted for use with this invention. Any suitable transducer can be used, including one, one and a half, and two-dimensional phased arrays of both PZT and other materials, whether planar, curved, or otherwise shaped.

Figure 16:
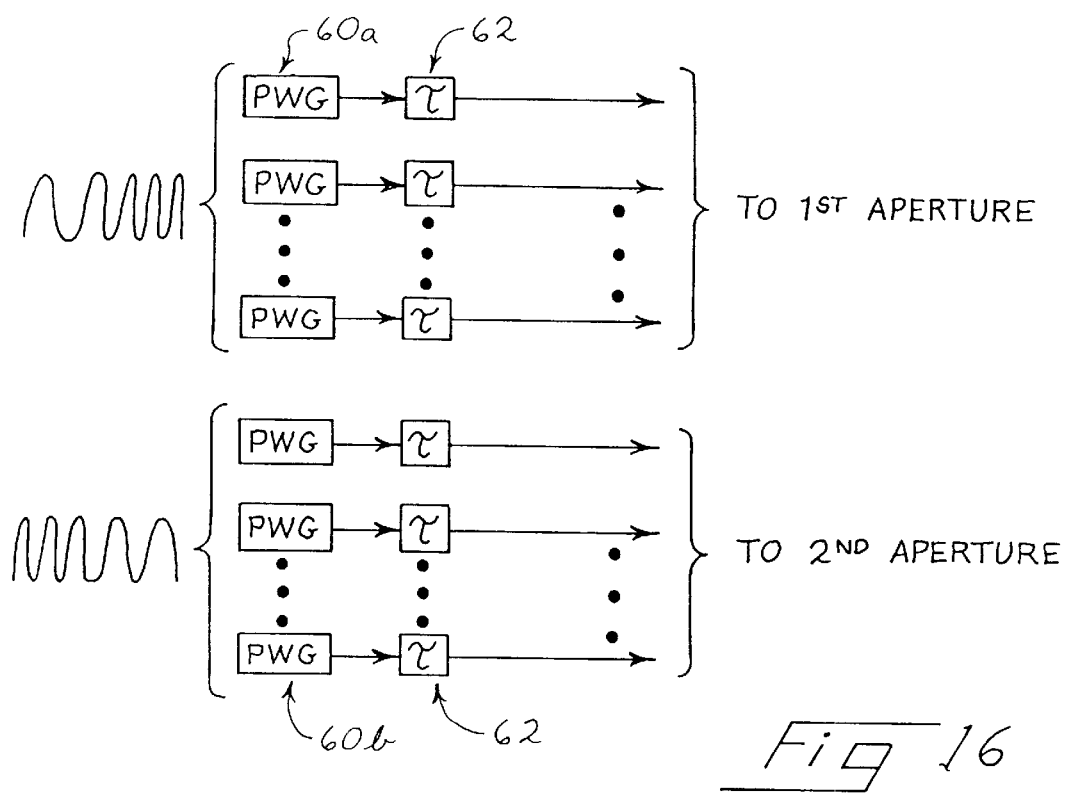
Figure 17:
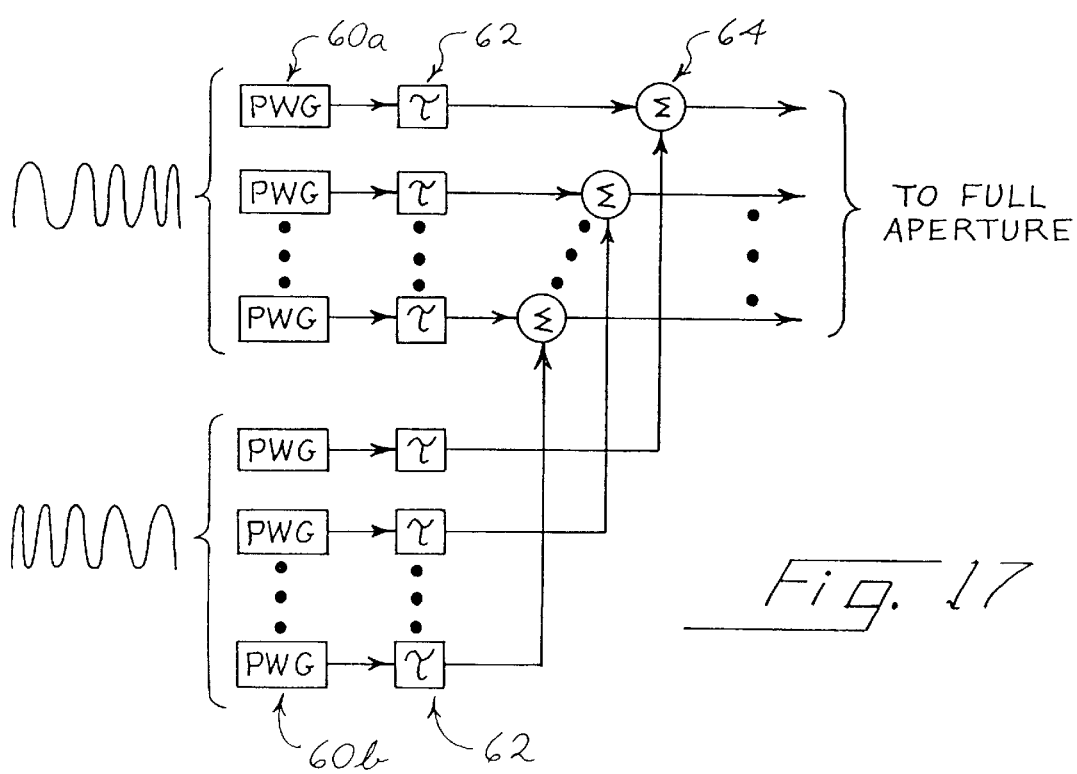

The transmitters can be formed using programmable waveform generators (PWG's) or impulse generators. FIGS. 16, 17 and 18 show three alternative transmitter embodiments using programmable waveform generators. In FIG. 16 the transmit beamformer is represented schematically by the delay units 62. In the embodiment of FIG. 16, the programmable waveform generators 60a generate coded transmit waveforms using a first code, and the programmable waveform generators 60b generate transmit waveforms that are coded using a second code, different from the first. Preferably, the codes used by the programmable waveform generators 60a, 60b are substantially orthogonal to minimize interference caused by the respective transmit beams. The transmit waveforms generated by the programmable waveform generators 60a and delayed by the delay units 62 are applied to a first subaperture of the transducer, and the transmit waveforms generated by the programmable waveform generators 60b and delayed by the delay units 62 are applied to a second subaperture of the transducer. The delay units 62 are programmed to introduce time delays that create the desired focal patterns for the respective transmit beams. In many cases this desired focal pattern will include a single point focus.

The embodiment of FIG. 17 is similar to that of FIG. 16, except that the transmit waveforms generated by the programmable waveform generators 60a, 60b are summed in summers 64 after time delay by the delay units 62. In this embodiment transmit waveforms using both the first code and the second code are both applied to the full aperture of the transducer.

FIG. 18 relates to a third embodiment in which the coded transmit waveforms from the programmable waveform generators 60a, delayed by the delay units 62, are applied to a first subaperture and the coded transmit waveforms generated by the programmable waveform generators 60b, delayed by the delay units 62, are applied to a second subaperture. In this case the first and second subapertures overlap partially and for this reason summers 64 sum the transmit waveforms from the respective programmable waveform generators 60a, 60b prior to applying the combined transmit waveforms to the transducer elements that are included in both subapertures.

FIG. 19 shows another embodiment that is similar to the embodiment of FIG. 16 in that separately coded transmit beams are launched from nonoverlapping first and second subapertures of the transducer. In the embodiment of FIG. 19, an impulse generator 66 applies an impulse to first and second coding filters 68a, 68b. The coding filters 68a, 68b respond to the impulse by generating respective coded transmit waveforms, which are applied to delay units 70 and then to the transducer elements of the respective subapertures.

FIGS. 16–19 provide examples of transmitters that use the same nonlinear phase modulation function across the entire aperture or subaperture associated with each respective beam. Thus, the nonlinear phase modulation function is spatially invariant across the respective aperture. This is quite different from the frequency dependent focus system described in Hossack et al. U.S. Pat. No. 5,608,690, assigned to the assignee of the present invention. In the system described in the Hossack et al. patent, the phase modulation function varies across the face of the transducer to produce the desired frequency dependent focus.

Figures 20, 21:
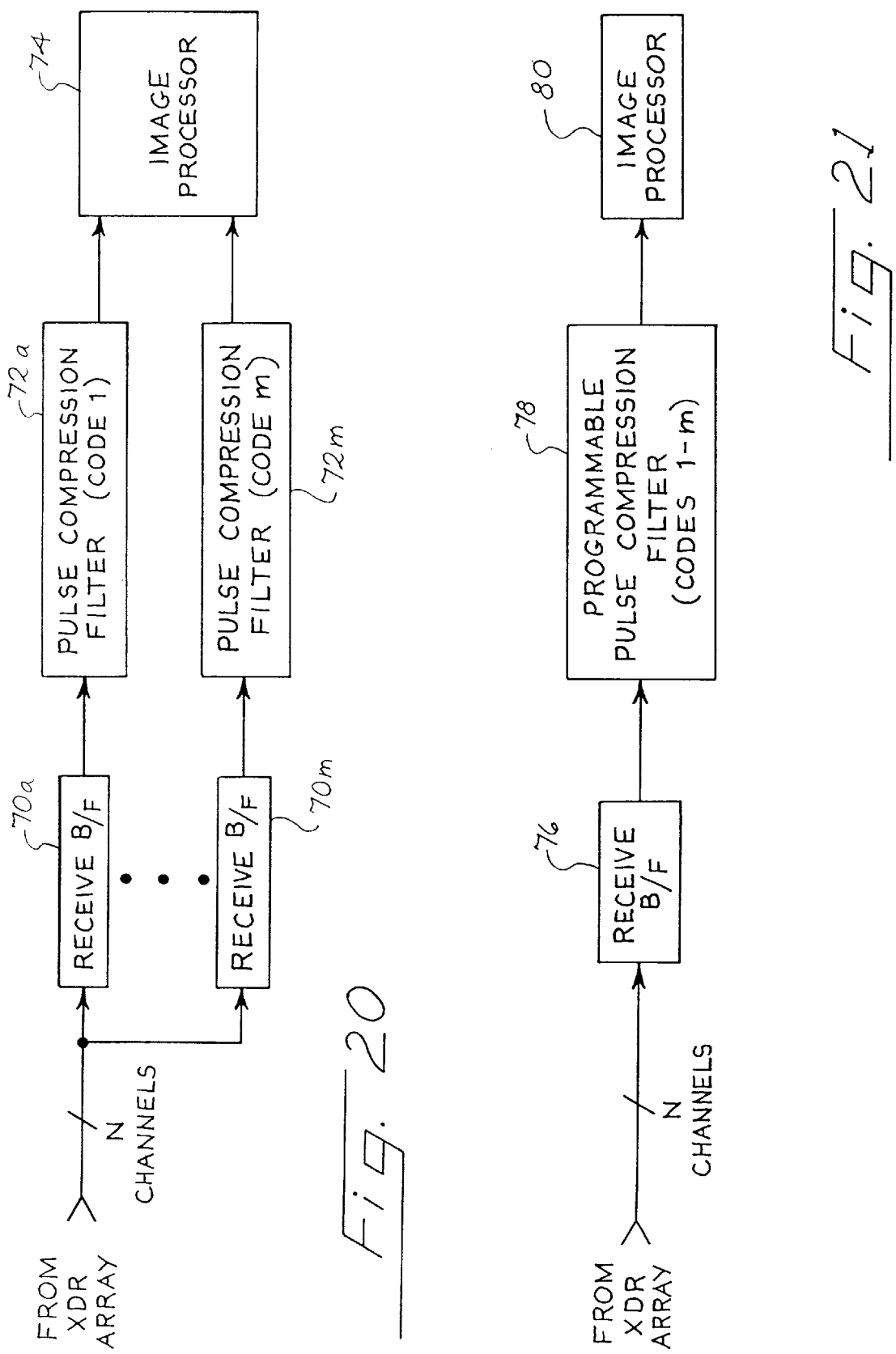
FIGS. 20 and 21 are block diagrams of alternative embodiments of a decoding receiver.

FIGS. 20 and 21 show two alternative architectures that can be used in the receiver. In FIG. 20 the receiver includes m separate receive beamformers 70a . . . 70m, and the beamformed receive signals are applied to m separate respective pulse compression filters 72a–72m. The output signals generated by the filters 72a–72m are applied to an image processor 74. This embodiment is an example of parallel pulse compression filters, and is similar to the embodiment of FIG. 1 in this regard.

The embodiment of FIG. 21 uses time interleaving techniques to reduce the number of hardware components in the receiver. In the embodiment of FIG. 21 there is a single receive beamformer 76 that beamforms echo signals from the transducer elements and applies the beamformed receive signal to a pulse compression filter 78. The pulse compression filter is preferably a programmable digital pulse compression filter that can quickly be programmed to any one of m different pulse compression codes. The output of the filter 78 is applied to an image processor 80. In the embodiment of FIG. 21, interleaving occurs at a scale of either the sampling frequency or the time interval between successive transmit events.

Concluding Remarks

It should be apparent from the foregoing that a number of improved methods and systems have been described that utilize coded transmit beams to enhance frame rate, SNR, or measurement accuracy.

As used herein, the term "transmit code" and "coded transmit beam" are intended broadly to refer to a transmit pulse with a nonlinear phase modulation in which the zero crossings of the pulse are unevenly spaced in time. Such pulses may or may not be amplitude modulated. Frequency modulated pulses such as chirp pulses are well-known examples of coded transmit beams, though as described above a wide variety of nonlinear phase modulation functions can be used to form a coded transmit beam within the scope of this invention.

The term "transmit event" is intended to refer to a single firing of a transducer. Thus, though a transmit event may extend over a considerable time period, all transducer elements on the transducer will not simultaneously remain at zero voltage for more than an instantaneous zero crossing time within a single transmit event.

The term "harmonic" as used herein is intended broadly to encompass integer harmonics, subharmonics and ultraharmonics. These, for example, may include harmonics of order 2, ½, and ⅔, respectively, but are not limited to these examples.

The foregoing detailed description has described only a few of the many forms that this invention can take. For this reason, this detailed description is intended only by way of illustration. It is only the following claims, including all equivalents, that are intended to define the scope of this invention.

What is claimed is:

1. An ultrasonic transmitting method for a phased-array transducer probe of a medical diagnostic ultrasonic imaging system, said method comprising:
   (a) launching a first coded ultrasonic transmit beam into a body along a first transmit beam direction, said first coded ultrasonic transmit beam modulated with a first code;
   (b) launching a second coded ultrasonic transmit beam into the body along a second transmit beam direction, spatially distinct from the first transmit beam direction, before the first transmit beam has left the tissue, said second coded ultrasonic transmit beam modulated with a second code, different from the first code;
   (c) acquiring receive signals from the body in response to the first and second transmit beams;
   (d) applying at least some of the receive signals to a first compression filter characterized by a first pulse compression function; and
   (e) applying at least some of the receive signals to a second compression filter characterized by a second pulse compression function, different from the first pulse compression function.

2. An ultrasonic transmitting method for a phased-array transducer probe of a medical diagnostic ultrasonic imaging system, said method comprising the following steps:
   (a) launching a first coded ultrasonic transmit beam with a dominant focus along a selected direction into a body, said first coded ultrasonic transmit beam modulated with a first code;
   (b) launching a second coded ultrasonic transmit beam with a similar focus alone the same direction into the body before the first transmit beam has left the tissue, said second coded ultrasonic transmit beam modulated with a second code, different from the first code;
   (c) acquiring receive signals from the body in response to the first and second transmit beams;
   applying at least some of the receive signals to a first compression filter characterized by a first pulse compression function; and
   (e) applying at least some of the receive signals to a second compression filter characterized by a second pulse compression function, different from the first pulse compression function.

3. The method of claim 2 wherein the imaging mode is selected from the group consisting of: B-mode imaging, color Doppler imaging, pulse inversion harmonic Doppler imaging, spectral Doppler imaging, motion processing imaging, strain imaging, 2-D imaging, 3-D imaging, imaging with at least one of fundamental, integer harmonic, fractional harmonic, subharmonic, and ultraharmonic frequencies, contrast agent imaging, tissue harmonic imaging, and combinations thereof.

4. The method of claim 1 or 2 further comprising:
   (f) image processing compressed receive signals generated by the first and second compression filters in an imaging mode.

5. A medical diagnostic ultrasonic imaging method comprising:
   (a) launching a first coded ultrasonic transmit beam into a body, said first coded ultrasonic transmit beam modulated with a first code;
   (b) launching a second coded ultrasonic transmit beam into the body before the first transmit beam has left the body, said second coded ultrasonic transmit beam modulated with a second code, different from the first code;
   (c) acquiring receive signals from the body in response to the first and second transmit beams;
   (d) applying at least some of the receive signals to a first compression filter characterized by a first pulse compression function;
   (e) applying at least some of the receive signals to a second compression filter characterized by a second pulse compression function, different from the first pulse compression function; and
   (f) image processing compressed receive signals generated by the first and second compression filters in an imaging mode;
   wherein the transmit beams are each characterized by a respective phase modulation function that is spatially invariant across a respective transducer aperture associated with each transmit beam; and
   wherein the imaging mode is selected from the group consisting of: color Doppler imaging using autocorrelation processing, pulse inversion harmonic Doppler imaging, spectral Doppler imaging, motion processing imaging, strain imaging, and combinations thereof.

6. The method of claim 1 or 2 wherein the imaging mode is characterized by at least one of 2-D imaging, 3-D imaging, harmonic frequency imaging, contrast agent imaging, and tissue harmonic imaging.

7. The method of claim 1, 2 or 5 wherein the first and second pulse compression functions are substantially matched in amplitude and phase to the first and second codes, respectively, for frequencies of interest at inputs to each compression filter.

8. The method of claim 1, 2 or 5 wherein the first and second pulse compression functions are substantially matched in phase to the first and second codes, respectively, for frequencies of interest at inputs to each compression filter.

9. The method of claim 8 wherein the first and second pulse compression functions are characterized by envelopes that are different than respective receive signal envelopes at inputs to each compression filter.

10. The method of claim 8 wherein the first and second pulse compression functions are each substantially uniform in amplitude.

11. The method of claim 1, 2 or 5 wherein at least one of the first and second pulse compression functions provides amplitude modulation that is symmetric in time about half an envelope duration.

12. The method of claim 1, 2 or 5 wherein at least one of the first and second pulse compression functions provides amplitude modulation that is asymmetric in time about half an envelope duration.

13. The method of claim 1, 2 or 5 wherein at least one of the first and second pulse compression functions provides amplitude modulation that is a continuous function of time.

14. The method of claim 1, 2 or 5 wherein at least one of the first and second pulse compression functions provides amplitude modulation that is a discontinuous function of time.

15. The method of claim 1, 2 or 5 wherein at least one of the first and second pulse compression functions provides phase modulation that is symmetric in time about half an envelope duration.

16. The method of claim 1, 2 or 5 wherein at least one of the first and second pulse compression functions provides phase modulation that is asymmetric in time about half an envelope duration.

17. The method of claim 1, 2 or 5 wherein at least one of the pulse compression functions provides a phase function versus frequency spectrum that is symmetric in frequency about a signal spectral peak.

18. The method of claim 1, 2 or 5 wherein at least one of the pulse compression functions provides a phase function versus frequency spectrum that is asymmetric in frequency about a signal spectral peak.

19. The method of claim 1, 2 or 5 wherein at least one of the codes is characterized by amplitude modulation.

20. The method of claim 1, 2 or 5 wherein at least one of the pulse compression functions is characterized by amplitude modulation.

21. The method of claim 1, 2 or 5 wherein at least one of the codes and the associated pulse compression function are both characterized by amplitude modulation.

22. The method of claim 1, 2 or 5 wherein at least one of the compression filters is characterized by an impulse response that varies as a function of time.

23. The method of claim 1, 2 or 5 wherein at least one of the compression filters is characterized by an impulse response that is constant over time.

24. The method of claim 1, 2 or 5 wherein the first and second filters operate in parallel.

25. The method of claim 1, 2 or 5 wherein the first and second filters operate sequentially in time.

26. A medical diagnostic ultrasonic imaging method comprising:

a) launching a coded ultrasonic transmit beam into a body;
b) acquiring receive signals from the body in response to the transmit beam;
c) applying the receive signals to a compression filter characterized by a pulse compression function; and
d) image processing compressed receive signals generated by the compression filter in an imaging mode;

wherein the transmit beam is characterized by a phase modulation function that is spatially invariant across a respective transducer aperture; and wherein the imaging mode is selected from the group consisting of color Doppler imaging using autocorrelation processing, pulse inversion harmonic Doppler imaging, spectral Doppler imaging, strain imaging, and combinations thereof.

27. The method of claim 26 wherein the transmit beam is modulated with a code, and wherein the pulse compression function is substantially matched in amplitude and phase to the code for frequencies of interest.

28. The method of claim 26 wherein the transmit beam is modulated with a code, and wherein the pulse compression function is substantially matched in phase to the code for frequencies of interest.

29. The method of claim 28 wherein the pulse compression function is substantially uniform in amplitude.

30. The method of claim 26 wherein the pulse compression function provides amplitude modulation that is symmetric in time about half an envelope duration.

31. The method of claim 26 wherein the pulse compression function provides amplitude modulation that is asymmetric in time about half an envelope duration.

32. The method of claim 26 wherein the pulse compression function provides amplitude modulation that is a continuous function in time.

33. The method of claim 26 wherein the pulse compression function provides amplitude modulation that is a discontinuous function of time.

34. The method of claim 26 wherein the pulse compression function provides phase modulation that is symmetric in time about half an envelope duration.

35. The method of claim 26 wherein the pulse compression function provides phase modulation that is asymmetric in time about half an envelope duration.

36. The method of claim 26 wherein the pulse compression function provides a phase function versus frequency spectrum that is symmetric in frequency about a signal spectral peak.

37. The method of claim 26 wherein the pulse compression function provides a phase function versus frequency spectrum that is asymmetric in frequency about a signal spectral peak.

38. The method of claim 26 wherein the transmit beam is modulated with a code characterized by amplitude modulation.

39. The method of claim 26 wherein the pulse compression function is characterized by amplitude modulation.

40. The method of claim 26 wherein the transmit beam is modulated with a code characterized by amplitude modulation, and wherein the pulse compression function is characterized by amplitude modulation.

41. The method of claim 26 wherein the compression filter is characterized by an impulse response that varies as a function of time.

42. The method of claim 26 wherein the compression filter is characterized by an impulse response that is constant over time.

43. A medical diagnostic ultrasonic imaging system comprising:
- at least one first pulse generator operative to generate a first set of coded transmit waveforms modulated with a first code and timed to form a first transmit beam along a first transmit beam direction;
- at least one second pulse generator operative to generate a second set of coded transmit waveforms modulated with a second code, different from the first code, and timed to form a second transmit beam along a second transmit beam direction, spatially distinct from the first transmit beam direction;
- a controller coupled with each of the first and second pulse generators and operative to initiate generation of both the first and second sets of coded transmit waveforms;
- a transducer probe comprising a plurality of transducer elements coupled with selected ones of the first and second pulse generations;
- a receiver coupled with the transducer elements, said receiver comprising first and second compression filters characterized by respective, distinct first and second pulse compression functions.

44. A medical diagnostic ultrasonic imaging system comprising:
- at least one first pulse generator operative to generate a first set of coded transmit waveforms modulated with a first code and timed to form a first transmit beam with a dominant focus;
- at least one second pulse generator operative to generate a second set of coded transmit waveforms modulated with a second code, different from the first code, and timed to form a second transmit beam with a similar focus;
- a controller coupled with each of the first and second pulse generators and operative to initiate generation of both the first and second sets of coded transmit waveforms;
- a transducer probe comprising a plurality of transducer elements coupled with selected ones of the first and second pulse generations;
- a receiver coupled with the transducer elements, said receiver comprising first and second compression filters characterized by respective, distinct first and second pulse compression functions.

45. The invention of claim 44 wherein the first and second sets of transmit waveforms are focused at different depths.

46. The invention of claim 43 or 44 wherein the first and second codes are substantially orthogonal to one another.

47. The invention of claim 43 or 44 wherein the controller is operative to initiate generation of both the first and second sets of coded transmit waveforms in a single transmit event.

48. The invention of claim 43 or 44 wherein the controller is operative to initiate generation of the first and second sets of coded transmit waveforms in separate transmit events.

49. The invention of claim 43 or 44 wherein the first set of transmit waveforms is associated with a first set of transducer elements and wherein the second set of transmit waveforms is associated with a second set of transducer elements.

50. The invention of claim 49 wherein the first and second sets of transducer elements do not overlap.

51. The invention of claim 49 wherein the first and second sets of transducer elements overlap.

52. The invention of claim 49 wherein the first and second sets of transducer elements are identical to one another.

53. The invention of claim 43 or 44 wherein the first and second sets of transmit waveforms are focused at a common depth.

54. The invention of claim 43 or 44 wherein the first and second pulse compression functions are substantially matched with the first and second codes, respectively.

55. The invention of claim 43 or 44 further comprising an image processor coupled to the receiver, said image processor operative to process compressed receive signals generated by the first and second compression filters in an imaging mode.

56. The invention of claim 55 wherein the imaging mode is selected from the group consisting of: B-mode imaging, color Doppler imaging, pulse inversion harmonic Doppler imaging, spectral Doppler imaging, motion processing imaging, strain imaging, 2-D imaging, 3-D imaging, imaging with at least one of fundamental integer harmonic, fractional harmonic, subharmonic, and ultraharmonic frequencies, contrast agent imaging, tissue harmonic imaging, and combinations thereof.

57. The invention of claim 56 wherein the imaging mode comprises motion processing imaging.

58. The method of claim 43 or 44 wherein the transducer probe comprises a plurality of active transducer elements, and wherein at least one of the first and second codes is phase modulated with a phase function versus frequency spectrum that is symmetric in frequency about a spectral peak of the respective transmit beam.

59. The method of claim 43 or 44, wherein the transducer probe comprises a plurality of active transducer elements, and wherein at least one of the first and second codes is phase modulated with a phase function versus frequency spectrum that is asymmetric in frequency about a spectral peak of the respective transmit beam.

60. A medical diagnostic ultrasonic imaging method comprising:
- (a) launching a plurality of coded ultrasonic transmit beams into a body, said transmit beams each characterized by a respective phase modulation function that is spatially invariant across a respective transducer aperture associated with each transmit beam;
- (b) acquiring a plurality of receive signals from the body in response to the transmit beams; and
- (c) motion detection processing the receive signals using at least one of an autocorrelation algorithm and an FFT algorithm.

61. The method of claim 60 wherein the transmit beams launched in (a) each comprise a single respective focus.

62. The method of claim 61 wherein each focus is a point focus.

63. The method of claim 60 wherein the transmit beams of (a) comprise a plurality of first transmit beams included in a single transmit event and characterized by separate respective phase modulation functions.

64. The method of claim 60 wherein (c) comprises color flow processing the receive signals.

65. The method of claim 64 wherein the transmit beams of (a) are characterized by at least two separate phase modulation functions.

66. The method of claim 65 wherein the at least two separate phase modulation functions are associated with separate respective transmit events.

67. The method of claim 60 wherein (c) comprises spectral Doppler processing the receive signals.

68. The method of claim 67 wherein the transmit beams of (a) are characterized by at least two separate phase modulation functions.

69. The method of claim 68 wherein the at least two separate phase modulation functions are associated with separate respective transmit events.

70. The method of claim 60 wherein the transmit beams are characterized by a fundamental frequency, and wherein (b) comprises acquiring the receive signals at a harmonic of the fundamental frequency.

71. The method of claim 60 wherein the phase modulation functions comprise at least two different phase modulation functions, each associated with a separate respective transmit event.

72. The method of claim 60 wherein the phase modulation functions comprise at least two different phase modulation functions, each associated with a separate respective scan line.

73. The method of claim 60 further comprising:
  (d) processing at least some of the receive signals in an imaging mode different from the motion detection processing of (c); and
  (e) combining processed receive signals from (c) and (d) for display.

74. The method of claim 60 wherein at least two of the transmit beams of (a) are characterized by spatially distinct foci and are launched in a common transmit event.

75. The method of claim 60 wherein at least two of the transmit beams of (a) are associated with separate respective transducer subapertures and are characterized by separate respective phase modulation functions.

76. A medical diagnostic ultrasonic imaging system comprising:
  means for launching a first coded ultrasonic transmit beam into a body, said first coded ultrasonic transmit beam modulated with a first code;
  means for launching a second coded ultrasonic transmit beam into the body before the first transmit beam has left the body, said second coded ultrasonic transmit beam modulated with a second code, different from the first code;
  means for acquiring receive signals from the body in response to the first and second transmit beams;
  means for applying at least some of the receive signals to a first compression filter characterized by a first pulse compression function;
  means for applying at least some of the receive signals to a second compression filter characterized by a second pulse compression function, different from the first pulse compression function; and
  means for image processing compressed receive signals generated by the first and second compression filters in an imaging mode;
  wherein the transmit beams are each characterized by a respective phase modulation function that is spatially invariant across a respective transducer aperture associated with each transmit beam; and
  wherein the imaging mode is selected from the group consisting of: color Doppler imaging using autocorrelation processing, pulse inversion harmonic Doppler imaging, spectral Doppler imaging, motion processing imaging, strain imaging, and combinations thereof.

77. An ultrasonic imaging method for a medial diagnostic ultrasonic imaging system, said method comprising:
  (a) transmitting a first coded ultrasonic transmit pulse into a body, said first coded ultrasonic pulse modulated with a first code;
  (b) acquiring receive signals from the body in response to the first transmit pulse;
  (c) transmitting at least a second coded transmit ultrasonic pulse into a body, said second coded ultrasonic transmit pulse differing from the pulse of (a) in at least one of transmit envelope phase and polarity;
  (d) acquiring receive signals from the body in response to the second transmit pulse;
  (e) applying at least some of the receive signals to at least one compression filter; and
  (f) combining compressed receive signals from (e) associated with the first and second transmit pulses.

78. The method of claim 77 further comprising:
  (g) image processing the combined signals from (f) in an imaging mode selected from the group consisting of: color Doppler imaging, spectral Doppler imaging, motion processing imaging, and strain imaging.

79. The method of claim 78 wherein (f) comprises:
  clutter filtering at least two received pulse-compressed signals before (g).

80. The method of claim 77, wherein (a) comprises applying a spatially invariant code to a plurality of active transducer elements of a transducer probe.

81. An ultrasonic transmitting method for a phased-array transducer probe of a medical diagnostic ultrasonic imaging system, said method comprising:
  (a) launching a first coded ultrasonic transmit beam into a body along a first transmit beam direction, said first coded ultrasonic transmit beam modulated with a first code;
  (b) launching a second coded ultrasonic transmit beam into the body along a second transmit beam direction, spatially distinct from the first transmit beam direction, before the first transmit beam has left the tissue, said second coded ultrasonic transmit beam modulated with a second code, different from the first code;
  wherein at least one of the first and second codes is phase modulated with a phase function versus frequency spectrum that is symmetric in frequency about a spectral peak of the respective transmit beam.

82. An ultrasonic transmitting method for a phased-array transducer probe of a medical diagnostic ultrasonic imaging system, said method comprising:
  (a) launching a first coded ultrasonic transmit beam into a body along a first transmit beam direction, said first coded ultrasonic transmit beam modulated with a first code;
  (b) launching a second coded ultrasonic transmit beam into the body along a second transmit beam direction, spatially distinct from the first transmit beam direction, before the first transmit beam has left the tissue, said second coded ultrasonic transmit beam modulated with a second code, different from the first code;
  wherein at least one of the first and second codes is phase modulated with a phase function versus frequency spectrum that is asymmetric in frequency about a spectral peak of the respective transmit beam.

83. An ultrasonic transmitting method for a phased-array transducer probe of a medical diagnostic ultrasonic imaging system, said method comprising steps:
  (a) launching a first coded ultrasonic transmit beam with a dominant focus along a selected direction into a body, said first coded ultrasonic transmit beam modulated with a first code;
  (b) launching a second coded ultrasonic transmit beam with a similar focus along the same direction into the body before the first transmit beam has left the tissue, said second coded ultrasonic transmit beam modulated with a second code, different from the first code;

wherein at least one of the first and second codes is phase modulated with a phase function versus frequency spectrum that is symmetric in frequency about a spectral peak of the respective transmit beam.

84. An ultrasonic transmitting method for a phased-array transducer probe of a medical diagnostic ultrasonic imaging system, said method comprising steps:

(a) launching a first coded ultrasonic transmit beam with a dominant focus along a selected direction into a body, said first coded ultrasonic transmit beam modulated with a first code;

(b) launching a second coded ultrasonic transmit beam with a similar focus along the same direction into the body before the first transmit beam has left the tissue, said second coded ultrasonic transmit beam modulated with a second code, different from the first code;

wherein at least one of the first and second codes is phase modulated with a phase function versus frequency spectrum that is asymmetric in frequency about a spectral peak of the respective transmit beam.

85. The method of claim 2, 83, 84 wherein the transducer probe comprises a plurality of transducer elements, wherein (a) and (b) comprise applying respective transmit waveforms to the elements, and wherein the transmit waveforms at each element from the first coded beam substantially overlap in time with the transmit waveforms from the second coded beam.

86. The method of claim 2, 83, 84 wherein the transducer probe comprises a plurality of transducer elements, wherein (a) and (b) comprise applying respective transmit waveforms to the elements, wherein the transmit waveforms at each element from the first coded beam do not overlap in time with the transmit waveforms from the second coded beam, and wherein the second coded beam transmit waveforms begin when the first coded beam transmit waveforms end.

87. The method of claim 2, 83, 84 wherein the transducer probe comprises a plurality of transducer elements, wherein (a) and (b) comprise applying respective transmit waveforms to the elements, wherein the transmit waveforms at each element from the first coded beam do not overlap in time with the transmit waveforms from the second coded beam, and wherein the second coded beam transmit waveforms begin a non-zero positive time after the first coded beam transmit waveforms.

88. The method of claim 1, 2, 81, 82, 83, or 84 wherein the first and second FM codes are substantially orthogonal.

89. The method of claim 1, 2, 81, 82, 83, or 84 wherein the first and second transmit beams are included in a single transmit event.

90. The method of claim 1, 2, 81, 82, 83, or 84 wherein first and second transmit beams are included in separate transmit events.

91. The method of claim 1, 2, 81, 82, 83, or 84 wherein the separate transmit events are spaced in time by less than a round trip echo time for a region of interest in the body.

92. The method of claim 1, 2, 81, 82, 83, or 84 wherein (a) comprises launching the first transmit beam with a first subaperture of a transducer probe, and wherein (b) comprises launching the second transmit beam with at least a second subaperture of the transducer probe, different from the first subaperture.

93. The method of claim 1, 2, 81, 82, 83, or 84 wherein (a) comprises launching the first transmit beam using a first set of transducer elements of the transducer probe and wherein (b) comprises launching the second transmit beam using at least a second set of transducer elements of the transducer probe.

94. The method of claim 93 wherein the first set does not overlap the second set.

95. The method of claim 93 wherein the first set overlaps the second set.

96. The method of claim 93 wherein the first set is identical to the second set.

97. The method of claim 1, 81, 82 wherein the first and second transmit beams are focused at different focal distances.

98. The method of claim 1, 2, 81, 82, 83, or 84 wherein the first and second transmit beams are focused at a common focal distance.

99. The method of claim 1, 2, 81, 82, 83, or 84 wherein (a) and (b) comprise launching said first and second coded ultrasonic transmit beams from respective first and second apertures of the phased array transducer probe, each of said apertures comprising a respective plurality of transducer elements.

100. The method of claim 17 wherein (a) and (b) comprise applying a respective focusing time delay profile for each aperture.

101. The method of claim 1, 2, 81, 82, 83, or 84 wherein at least one of the first and second codes is amplitude modulated with a modulation function that is symmetric in time about half an envelope duration.

102. The method of claim 1, 2, 81, 82, 83, or 84 wherein at least one of the first and second codes is amplitude modulated with a modulation function that is asymmetric in time about half an envelope duration.

103. The method of claim 1, 2, 81, 82, 83, or 84 wherein at least one of the first and second codes is amplitude modulated with a substantially uniform modulation function.

104. The method of claim 1, 2, 81, 82, 83, or 84 wherein at least one of the first and second codes is amplitude modulated with a substantially nonuniform modulation function.

105. The method of claim 1, 2, 81, 82, 83, or 84 wherein at least one of the first and second codes is amplitude modulated with a time-continuous modulation function.

106. The method of claim 1, 2, 81, 82, 83, or 84 wherein at least one of the first and second codes is amplitude modulated with a time-discontinuous modulation function.

107. The method of claim 1, 2, 81, 82, 83, or 84 wherein at least one of the first and second codes is phase modulated with a phase modulation function that is symmetric in time about half an envelope duration.

108. The method of claim 1, 2, 81, 82, 83, or 84 wherein at least one of the first and second codes is phase modulated with a phase modulation function that is asymmetric in time about half an envelope duration.

109. The method of claim 1, 2, 43, 44, 81, 82, 83 or 84 wherein at least one of the first and second codes is spatially invariant across the plurality of active transducer elements.

* * * * *

UNITED STATES PATENT AND TRADEMARK OFFICE
CERTIFICATE OF CORRECTION

PATENT NO. : 6,213,947 B1
DATED : April 10, 2001
INVENTOR(S) : Patrick Phillips

It is certified that error appears in the above-identified patent and that said Letters Patent is hereby corrected as shown below:

Column 8,
Line 23, equation (1), delete "$l(t)=[P\{X_{tx}(t)*h(t)\}*\theta(t)*h_{rx}(t)]d(t)*X_{rx}(t)$" and substitute -- $l(t)=[P\{X_t(t)*h_{tx}(t)\}*\theta(t)*h_{rx}(t)]d(t)*X_{rx}(t)$ -- in its place.
Line 47, delete "$X'_{tx}(t) = \text{Re}\{a(t)e^{j\phi(t)}e^{j2\pi f_m t}\}$," and substitute -- $X'_{tx}(t) = \text{Re}\{a(t)e^{j\phi(t)}e^{j2\pi f_m t}\}$, --  in its place.

Column 10,
Line 28, delete "$n(t) = a^2(t)e^{j2\pi(t)}$" and substitute -- $n(t) = a^2(t)e^{j2\phi(t)}$ -- in its place.

Column 14,
Line 13, delete "a (t)," and substitute -- $\alpha$ (t), -- in its place.
Line 24, delete "WFM" and substitute -- $W_{FM}$ -- in its place.

Column 17,
Line 8, delete "09/287,603," and substitute -- 09/282,603, -- in its place.

Column 18,
Line 9, delete "09/282,306" and substitute -- 09/282,396 -- in its place.

Column 21,
Line 42, delete "to" and substitute -- $t_1$ -- in its place.

Column 23,
Line 14, delete "$\phi'(t) = \phi(t)+(n-1)$" and substitute -- $\phi'(t)=\phi(t)+(n-1)\pi$ -- in its place.

Column 25,
Line 45, delete "scattefed" and substitute -- scattered -- in its place.

Column 27,
Line 51, start a new paragraph with the words "As suggested above,".

UNITED STATES PATENT AND TRADEMARK OFFICE
CERTIFICATE OF CORRECTION

PATENT NO. : 6,213,947 B1
DATED : April 10, 2001
INVENTOR(S) : Patrick Phillips

It is certified that error appears in the above-identified patent and that said Letters Patent is hereby corrected as shown below:

<u>Column 30,</u>
Line 12, delete "applying" and substitute -- (d) applying -- in its place.

Signed and Sealed this

Third Day of June, 2003

JAMES E. ROGAN
*Director of the United States Patent and Trademark Office*